United States Patent
Crapser et al.

(10) Patent No.: US 7,837,958 B2
(45) Date of Patent: Nov. 23, 2010

(54) DEVICE AND METHODS OF PROVIDING AIR PURIFICATION IN COMBINATION WITH SUPERFICIAL FLOOR CLEANING

(75) Inventors: James R. Crapser, Racine, WI (US); Thomas P. Gasper, Germantown, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 184 days.

(21) Appl. No.: 11/667,984

(22) PCT Filed: Nov. 22, 2005

(86) PCT No.: PCT/US2005/042547
§ 371 (c)(1),
(2), (4) Date: Aug. 14, 2007

(87) PCT Pub. No.: WO2006/058125
PCT Pub. Date: Jun. 1, 2006

(65) Prior Publication Data
US 2008/0206092 A1 Aug. 28, 2008

Related U.S. Application Data

(60) Provisional application No. 60/630,339, filed on Nov. 23, 2004.

(51) Int. Cl.
*A61L 9/00* (2006.01)
*A47L 5/00* (2006.01)

(52) U.S. Cl. ............ 422/291; 422/120; 422/123; 422/105; 15/319

(58) Field of Classification Search ............ 422/5, 422/22, 120, 123, 186, 186.04, 105, 291; 15/1.51, 319, 321
See application file for complete search history.

(56) References Cited

U.S. PATENT DOCUMENTS 848,974 A 4/1907 Crossman (Continued)

FOREIGN PATENT DOCUMENTS

CA 2531305 10/2006

(Continued)

OTHER PUBLICATIONS

Svetlana Domnitecheva: "Smart Vacuum Cleaner—An Autonomous Location-Aware Cleaning Device" International Conference on Ubiquitous Computing (Online) Sep. 10, 2004 Nottingham, England Retrieved from the Internet: URL:http://ubicomp.org/ubicomp2004/adjunct/posters/domnitch.pdf.

(Continued)

*Primary Examiner*—Sean E Conley

(57) ABSTRACT

The present invention is a system for and method of providing an autonomously mobile air purifier and surface cleaner in combination with a source of air fragrance in a single device for home or office use. The autonomously mobile air and surface cleaner and fragrancing system includes an air purifier, a fragrancer, a floor cleaner, an input means, a power system, operational and auxiliary sensors, robotics that drive and steer the device, and a central controller operatively connected to each of the aforementioned items to control the operation of the device. The present invention also provides a method for the operation of the device using the air purifier, fragrancer, floor cleaner and robotics to clean a room, and for modifying the operation of the device in response to signals sent from the sensors or from the input means.

20 Claims, 24 Drawing Sheets

U.S. PATENT DOCUMENTS

| | | |
|---|---|---|
| 2,227,104 A | 12/1940 | Parker |
| 2,243,935 A | 6/1941 | Williamson |
| 2,407,408 A | 9/1946 | Erickson |
| 2,476,537 A | 7/1947 | Erickson |
| 2,483,169 A | 9/1949 | Anderson |
| 2,506,077 A | 5/1950 | Goldsmith |
| 2,584,515 A | 2/1952 | Udell |
| 2,655,680 A | 10/1953 | Geerin |
| 2,960,714 A | 11/1960 | Senne |
| 2,963,731 A | 12/1960 | Hoots |
| 5,074,008 A | 12/1991 | Palomino, Jr. |
| 5,077,863 A | 1/1992 | Rench |
| 5,109,566 A | 5/1992 | Kobayashi et al. |
| 5,127,123 A | 7/1992 | Belanger |
| 5,165,064 A | 11/1992 | Mattaboni |
| 5,203,047 A | 4/1993 | Lynn |
| 5,214,822 A | 6/1993 | Sakurai et al. |
| 5,279,672 A | 1/1994 | Betker et al. |
| 5,292,582 A | 3/1994 | Gibbs et al. |
| 5,293,955 A | 3/1994 | Lee |
| 5,297,311 A | 3/1994 | Puri |
| 5,309,592 A | 5/1994 | Hiratsuka |
| 5,327,609 A | 7/1994 | Bierma et al. |
| 5,341,540 A | 8/1994 | Soupert et al. |
| 5,399,381 A | 3/1995 | Randall |
| 5,440,216 A * | 8/1995 | Kim ............................ 318/587 |
| 5,454,129 A | 10/1995 | Kell |
| 5,594,971 A | 1/1997 | Nelson |
| 5,613,261 A | 3/1997 | Kawakami et al. |
| 5,621,291 A | 4/1997 | Lee |
| 5,634,237 A | 6/1997 | Paranjpe |
| 5,636,402 A | 6/1997 | Kubo et al. |
| 5,643,047 A | 7/1997 | Beckett et al. |
| 5,646,494 A | 7/1997 | Han |
| 5,682,313 A | 10/1997 | Edlund et al. |
| 5,720,077 A | 2/1998 | Nakamura et al. |
| 5,735,959 A | 4/1998 | Kubo et al. |
| 5,815,880 A | 10/1998 | Nakanishi |
| 5,825,981 A | 10/1998 | Matsuda |
| 5,883,582 A | 3/1999 | Bowers et al. |
| 5,894,621 A | 4/1999 | Kubo |
| 5,896,611 A | 4/1999 | Haaga |
| 5,933,900 A | 8/1999 | Wang |
| 5,935,179 A | 8/1999 | Kleiner et al. |
| 5,940,928 A | 8/1999 | Erko |
| 5,947,225 A | 9/1999 | Kawakami et al. |
| 5,974,626 A | 11/1999 | Wood et al. |
| 5,991,951 A | 11/1999 | Kubo et al. |
| 5,995,884 A | 11/1999 | Allen et al. |
| 5,996,167 A | 12/1999 | Close |
| 5,998,953 A | 12/1999 | Nakamura et al. |
| 6,012,618 A | 1/2000 | Matsuo |
| 6,046,565 A | 4/2000 | Thorne |
| 6,049,745 A | 4/2000 | Douglas et al. |
| 6,099,091 A | 8/2000 | Campbell |
| 6,102,278 A | 8/2000 | Rothas |
| 6,105,192 A | 8/2000 | Deiterman et al. |
| 6,112,996 A | 9/2000 | Matsuo |
| 6,124,694 A | 9/2000 | Bancroft et al. |
| 6,138,063 A | 10/2000 | Himeda |
| 6,142,252 A | 11/2000 | Kinto et al. |
| 6,170,740 B1 | 1/2001 | Clark |
| 6,199,610 B1 | 3/2001 | Yanagawa |
| 6,212,725 B1 | 4/2001 | Porat |
| 6,223,378 B1 | 5/2001 | Watellier |
| 6,255,793 B1 | 7/2001 | Peless et al. |
| 6,295,687 B1 | 10/2001 | Dehart |
| 6,301,738 B1 | 10/2001 | Deiterman et al. |
| 6,311,356 B1 | 11/2001 | Wang |
| 6,324,714 B1 | 12/2001 | Walz et al. |
| 6,338,013 B1 | 1/2002 | Ruffner |
| 6,346,884 B1 | 2/2002 | Uozumi et al. |
| 6,370,452 B1 | 4/2002 | Pfister |
| 6,453,223 B1 | 9/2002 | Kelly et al. |
| 6,459,966 B2 | 10/2002 | Nakano et al. |
| 6,463,360 B1 | 10/2002 | Terada et al. |
| 6,481,515 B1 | 11/2002 | Kirkpatrick et al. |
| 6,532,404 B2 | 3/2003 | Colens |
| 6,532,619 B2 | 3/2003 | Kasper et al. |
| 6,548,982 B1 | 4/2003 | Papanikolopoulos et al. |
| 6,571,415 B2 | 6/2003 | Gerber et al. |
| 6,574,549 B2 | 6/2003 | Cato et al. |
| 6,591,216 B1 | 7/2003 | Magnussen |
| 6,594,844 B2 | 7/2003 | Jones |
| 6,599,844 B2 | 7/2003 | Koh et al. |
| 6,601,265 B1 | 8/2003 | Burlington |
| 6,611,738 B2 | 8/2003 | Ruffner |
| 6,622,088 B2 | 9/2003 | Hood |
| 6,633,150 B1 | 10/2003 | Wallach et al. |
| 6,658,325 B2 | 12/2003 | Zweig |
| 6,667,592 B2 | 12/2003 | Jacobs et al. |
| 6,671,592 B1 | 12/2003 | Bisset et al. |
| 6,690,134 B1 | 2/2004 | Jones et al. |
| 6,705,522 B2 | 3/2004 | Gershman et al. |
| 6,741,054 B2 | 5/2004 | Koselka et al. |
| 6,764,373 B1 | 7/2004 | Osawa et al. |
| 6,779,217 B2 | 8/2004 | Fisher |
| 6,809,490 B2 | 10/2004 | Jones et al. |
| 6,810,305 B2 | 10/2004 | Kirkpatrick, Jr. |
| 6,859,976 B2 | 3/2005 | Plankenhorn |
| 6,883,201 B2 | 4/2005 | Jones et al. |
| 6,904,335 B2 | 6/2005 | Solomon |
| 6,925,679 B2 | 8/2005 | Wallach et al. |
| 6,938,298 B2 | 9/2005 | Aasen |
| 6,941,199 B1 | 9/2005 | Bottomley et al. |
| 6,956,348 B2 | 10/2005 | Landry et al. |
| 6,966,098 B2 | 11/2005 | Sako et al. |
| 6,999,850 B2 | 2/2006 | McDonald |
| 7,013,527 B2 | 3/2006 | Thomas, Sr. et al. |
| 7,024,278 B2 | 4/2006 | Chiappetta et al. |
| 7,053,580 B2 | 5/2006 | Aldred |
| 7,054,716 B2 | 5/2006 | McKee et al. |
| 7,066,291 B2 | 6/2006 | Martins et al. |
| 7,079,923 B2 | 7/2006 | Abramson et al. |
| 7,082,350 B2 | 7/2006 | Skoog |
| 7,085,624 B2 | 8/2006 | Aldred et al. |
| 7,089,099 B2 | 8/2006 | Shostak et al. |
| 7,103,460 B1 | 9/2006 | Breed |
| 7,113,847 B2 | 9/2006 | Chmura et al. |
| 7,133,746 B2 | 11/2006 | Abramson et al. |
| 7,155,308 B2 | 12/2006 | Jones |
| 7,162,056 B2 | 1/2007 | Burl et al. |
| 7,162,338 B2 | 1/2007 | Goncalves et al. |
| 7,167,775 B2 | 1/2007 | Abramson et al. |
| 7,170,252 B2 | 1/2007 | Maeki |
| 7,173,391 B2 | 2/2007 | Jones et al. |
| 7,177,737 B2 | 2/2007 | Karlsson et al. |
| 7,184,586 B2 | 2/2007 | Jeon et al. |
| 7,188,000 B2 | 3/2007 | Chiappetta et al. |
| 7,197,374 B2 | 3/2007 | Silverbrook et al. |
| 7,237,298 B2 | 7/2007 | Reindle et al. |
| 7,248,951 B2 | 7/2007 | Hulden |
| 7,251,853 B2 | 8/2007 | Park et al. |
| 7,272,467 B2 | 9/2007 | Goncalves et al. |
| 7,275,280 B2 | 10/2007 | Haegermarck et al. |
| 7,288,912 B2 | 10/2007 | Landry et al. |
| 7,320,149 B1 | 1/2008 | Huffman et al. |
| 7,332,890 B2 | 2/2008 | Cohen et al. |
| 7,343,222 B2 | 3/2008 | Solomon |
| 7,346,428 B1 | 3/2008 | Huffman et al. |
| 7,359,766 B2 | 4/2008 | Jeon et al. |
| 7,388,343 B2 | 6/2008 | Jones et al. |
| 7,389,156 B2 | 6/2008 | Ziegler et al. |
| 7,389,166 B2 | 6/2008 | Harwig et al. |

| | | |
|---|---|---|
| 7,412,748 B2 | 8/2008 | Lee et al. |
| 7,430,455 B2 | 9/2008 | Casey et al. |
| 7,438,766 B2 | 10/2008 | Song et al. |
| 7,441,298 B2 | 10/2008 | Svendsen et al. |
| 7,444,206 B2 | 10/2008 | Abramson et al. |
| 7,448,113 B2 | 11/2008 | Jones et al. |
| 7,450,367 B2 | 11/2008 | Frank et al. |
| 2001/0027360 A1 | 10/2001 | Nakano et al. |
| 2001/0047231 A1 | 11/2001 | Peless et al. |
| 2001/0047559 A1 | 12/2001 | Graham et al. |
| 2001/0049855 A1 | 12/2001 | Massaro |
| 2002/0002751 A1 | 1/2002 | Fisher |
| 2002/0011813 A1 | 1/2002 | Koselka et al. |
| 2002/0016649 A1 | 2/2002 | Jones |
| 2002/0050016 A1 | 5/2002 | Willman et al. |
| 2002/0066149 A1 | 6/2002 | Gerber et al. |
| 2002/0100494 A1 | 8/2002 | Brown et al. |
| 2002/0132752 A1 | 9/2002 | Caruthers, Jr. |
| 2002/0156556 A1 | 10/2002 | Ruffner |
| 2002/0174506 A1 | 11/2002 | Wallach et al. |
| 2003/0009270 A1 | 1/2003 | Breed |
| 2003/0014186 A1 | 1/2003 | Adams, Jr. et al. |
| 2003/0025472 A1 | 2/2003 | Jones et al. |
| 2003/0060928 A1 | 3/2003 | Abramson et al. |
| 2003/0080901 A1 | 5/2003 | Piotrowski |
| 2003/0102014 A1 | 6/2003 | Yoshino |
| 2003/0120389 A1 | 6/2003 | Abramson et al. |
| 2003/0126701 A1 | 7/2003 | Aasen |
| 2003/0149676 A1 | 8/2003 | Kasabov |
| 2003/0159223 A1 | 8/2003 | Plankenhorn |
| 2003/0234730 A1 | 12/2003 | Arms |
| 2004/0002305 A1 | 1/2004 | Byman-Kivivuori et al. |
| 2004/0031111 A1 | 2/2004 | Porchia et al. |
| 2004/0031113 A1 | 2/2004 | Wosewick et al. |
| 2004/0031121 A1 | 2/2004 | Martin et al. |
| 2004/0034466 A1 | 2/2004 | Hood |
| 2004/0049877 A1 | 3/2004 | Jones et al. |
| 2004/0143930 A1 | 7/2004 | Haegermarck |
| 2004/0162227 A1 | 8/2004 | Caruthers, Jr. |
| 2004/0187249 A1 | 9/2004 | Jones et al. |
| 2004/0193322 A1 | 9/2004 | Pirjanian et al. |
| 2004/0195330 A1 | 10/2004 | Silverbrook et al. |
| 2004/0204792 A1 | 10/2004 | Taylor et al. |
| 2004/0244138 A1 | 12/2004 | Taylor et al. |
| 2005/0017181 A1 | 1/2005 | Kearfott et al. |
| 2005/0022273 A1 | 1/2005 | Maeki |
| 2005/0022331 A1* | 2/2005 | Kim et al. ................. 15/319 |
| 2005/0156562 A1 | 7/2005 | Cohen et al. |
| 2005/0162119 A1 | 7/2005 | Landry et al. |
| 2005/0166354 A1 | 8/2005 | Uehigashi |
| 2005/0166355 A1 | 8/2005 | Tani |
| 2005/0171636 A1 | 8/2005 | Tani |
| 2005/0171644 A1 | 8/2005 | Tani |
| 2005/0188494 A1 | 9/2005 | Takenaka |
| 2005/0217042 A1 | 10/2005 | Reindle |
| 2005/0218852 A1 | 10/2005 | Landry et al. |
| 2005/0229340 A1 | 10/2005 | Sawalski et al. |
| 2006/0074525 A1 | 4/2006 | Close et al. |
| 2006/0085095 A1 | 4/2006 | Reindle et al. |
| 2006/0155398 A1 | 7/2006 | Hoffberg et al. |
| 2006/0184293 A1 | 8/2006 | Konandreas et al. |
| 2006/0190132 A1 | 8/2006 | Morse et al. |
| 2006/0190133 A1 | 8/2006 | Konandreas et al. |
| 2006/0190134 A1 | 8/2006 | Ziegler et al. |
| 2006/0190146 A1 | 8/2006 | Morse et al. |
| 2006/0200281 A1 | 9/2006 | Ziegler et al. |
| 2006/0236492 A1 | 10/2006 | Sudo |
| 2006/0238156 A1 | 10/2006 | Kim |
| 2006/0288519 A1 | 12/2006 | Jaworski et al. |
| 2006/0293794 A1 | 12/2006 | Harwig et al. |
| 2006/0293809 A1 | 12/2006 | Harwig et al. |
| 2007/0016328 A1 | 1/2007 | Ziegler et al. |
| 2007/0028574 A1 | 2/2007 | Yan |
| 2007/0042716 A1 | 2/2007 | Goodall et al. |
| 2007/0061040 A1 | 3/2007 | Augenbraun et al. |
| 2007/0061041 A1 | 3/2007 | Zweig |
| 2007/0069680 A1 | 3/2007 | Landry et al. |
| 2007/0100500 A1 | 5/2007 | Abramson et al. |
| 2007/0131822 A1 | 6/2007 | Stallard |
| 2007/0179670 A1 | 8/2007 | Chiappetta et al. |
| 2007/0208442 A1 | 9/2007 | Perrone |
| 2007/0234492 A1 | 10/2007 | Svendsen et al. |
| 2007/0244610 A1 | 10/2007 | Ozick et al. |
| 2007/0250212 A1 | 10/2007 | Halloran et al. |
| 2007/0260394 A1 | 11/2007 | Dean |
| 2007/0262884 A1 | 11/2007 | Goncalves et al. |
| 2007/0266508 A1 | 11/2007 | Jones et al. |
| 2007/0272463 A1 | 11/2007 | Yu et al. |
| 2007/0285041 A1 | 12/2007 | Jones et al. |
| 2007/0290828 A1 | 12/2007 | Choi et al. |
| 2008/0000041 A1 | 1/2008 | Jones et al. |
| 2008/0000042 A1 | 1/2008 | Jones et al. |
| 2008/0001566 A1 | 1/2008 | Jones et al. |
| 2008/0007193 A1 | 1/2008 | Jones et al. |
| 2008/0016631 A1 | 1/2008 | Casey et al. |
| 2008/0039974 A1 | 2/2008 | Sandin et al. |
| 2008/0047092 A1 | 2/2008 | Schnittman et al. |
| 2008/0051953 A1 | 2/2008 | Jones et al. |
| 2008/0056933 A1 | 3/2008 | Moore et al. |
| 2008/0058987 A1 | 3/2008 | Ozick et al. |
| 2008/0066257 A1 | 3/2008 | Sun et al. |
| 2008/0084174 A1 | 4/2008 | Jones et al. |
| 2008/0086236 A1 | 4/2008 | Saito et al. |
| 2008/0091303 A1 | 4/2008 | Jung et al. |
| 2008/0091304 A1 | 4/2008 | Ozick et al. |
| 2008/0091305 A1 | 4/2008 | Svendsen et al. |
| 2008/0097645 A1 | 4/2008 | Abramson et al. |
| 2008/0109126 A1 | 5/2008 | Sandin et al. |
| 2008/0127445 A1 | 6/2008 | Konandreas et al. |
| 2008/0127446 A1 | 6/2008 | Ziegler et al. |
| 2008/0134457 A1 | 6/2008 | Morse et al. |
| 2008/0134458 A1 | 6/2008 | Ziegler et al. |
| 2008/0140255 A1 | 6/2008 | Ziegler et al. |
| 2008/0141485 A1 | 6/2008 | Kim et al. |
| 2008/0150466 A1 | 6/2008 | Landry et al. |
| 2008/0155768 A1 | 7/2008 | Ziegler et al. |
| 2008/0172824 A1 | 7/2008 | Yun et al. |
| 2008/0174268 A1 | 7/2008 | Koo et al. |
| 2008/0183349 A1 | 7/2008 | Abramson et al. |
| 2008/0184518 A1 | 8/2008 | Taylor et al. |
| 2008/0188984 A1 | 8/2008 | Harwig et al. |
| 2008/0191653 A1 | 8/2008 | Han et al. |
| 2008/0201895 A1 | 8/2008 | Kim et al. |
| 2008/0229528 A1 | 9/2008 | Chen et al. |
| 2008/0235897 A1 | 10/2008 | Kim et al. |
| 2008/0249661 A1 | 10/2008 | Hong et al. |
| 2008/0271273 A1 | 11/2008 | Reindle |
| 2008/0271278 A1 | 11/2008 | Jang |
| 2008/0276407 A1 | 11/2008 | Schnittman et al. |
| 2008/0276408 A1 | 11/2008 | Gilbert, Jr. et al. |
| 2008/0281470 A1 | 11/2008 | Gilbert, Jr. et al. |
| 2008/0281481 A1 | 11/2008 | Abramson et al. |

FOREIGN PATENT DOCUMENTS

| | | |
|---|---|---|
| DE | 19521358 | 9/1996 |
| DE | 10000407 A1 | 7/2001 |
| DE | 20116069 | 12/2001 |
| DE | 10346216 | 9/2004 |
| EP | 1027855 A2 | 8/2000 |
| EP | 1172719 A1 | 1/2002 |
| EP | 1224899 A2 | 7/2002 |
| EP | 1921572 | 5/2008 |
| FR | 850321 | 12/1939 |
| FR | 2446104 A1 | 8/1980 |
| GB | 2352486 | 1/2001 |

| | | |
|---|---|---|
| GB | 2404139 | 1/2005 |
| GB | 2409966 | 7/2005 |
| JP | 05095883 | 4/1993 |
| JP | 05250032 | 9/1993 |
| JP | 09145392 | 6/1997 |
| JP | 3395874 | 2/1998 |
| JP | 2001315674 | 11/2001 |
| JP | 2005141636 | 2/2005 |
| KR | 2006032333 | 4/2006 |
| KR | 619750 | 9/2006 |
| WO | WO 97/41451 | 11/1997 |
| WO | WO 00/04430 A1 | 1/2000 |
| WO | WO 0038029 | 6/2000 |
| WO | WO 01/37060 | 5/2001 |
| WO | WO 01/82766 A2 | 11/2001 |
| WO | WO 02/00819 | 1/2002 |
| WO | WO 02/39864 A1 | 5/2002 |
| WO | WO 02/101477 A2 | 12/2002 |
| WO | WO 2004/063883 | 7/2004 |
| WO | WO 2005/077244 | 8/2005 |
| WO | WO 2006/089307 | 8/2006 |
| WO | WO 2007/024460 | 3/2007 |
| WO | WO 2007/065030 | 6/2007 |
| WO | WO 2007/065031 | 6/2007 |
| WO | WO 2007/065033 | 6/2007 |
| WO | WO 2007/100756 | 9/2007 |
| WO | WO 2007/109624 | 9/2007 |
| WO | WO 2007/109627 | 9/2007 |
| WO | WO 2008/060690 | 5/2008 |

OTHER PUBLICATIONS

Jurgen Bohn and Friedemann Mattern: "Super-distributed RFID Tag Infrastructures" Second European Symposium, EUSAI 2004 (Online) Nov. 1, 2004 Eindhoven, The Netherlands Retrieved from the Internet: URL :http//www.springerlink.com/content/lrgp441x6mcf3ktm/fulltext.pdf.
International Search Report Opinion of PCT/US2006/025037.

* cited by examiner

Autonomously mobile air purifier 100

DEVICE AND METHODS OF PROVIDING AIR PURIFICATION IN COMBINATION WITH SUPERFICIAL FLOOR CLEANING

CROSS-REFERENCE TO RELATED APPLICATION

This application claims the benefit of U.S. Provisional Application Ser. No. 60/630,339, filed Nov. 23, 2004.

FIELD OF THE INVENTION

The present invention relates to autonomous and mobile cleaning devices. In particular, this invention relates to an autonomously mobile cleaning device that provides air purification or freshening, with an optional air fragrance feature, in combination with surface cleaning.

BACKGROUND OF THE INVENTION

The increase in awareness of the health risks inherent in air pollution recently has caused many people to reassess the quality of their indoor air and environment. Recent Environmental Protection Agency studies indicate that indoor air pollution levels could be 2-5 times higher than the ambient outdoor air pollution level. It is estimated by some that, on rare occasions, these indoor air pollution levels can be 100 times higher than outdoor air pollution levels. This is an increasingly important matter that must be addressed, because many people, especially infants and the elderly, spend more than 90% of their time indoors. Some of these indoor pollutants could also be contributing factors to frequent and unexplained headaches or sleepless nights that afflict numerous persons within the general population.

There are numerous devices in the prior art that are designed and manufactured for purifying indoor air. With more homes and offices becoming better insulated, an objective of air purifiers is to clear the indoor air of common pollutants, including dust, smoke, pollen, bacteria, soot, mold spores, animal dander, and other microscopic irritants, and thereby create a clean, healthy, fresh, and pleasant environment. Some of these devices generate ions by using complicated wire grid arrays or high voltage electrode arrays. Some use fans and similar devices for moving air. Some of these prior art devices are mounted in large housings that contain fans, filters, and other complicated moving parts. Often, the devices become clogged with pollutants, which requires disassembly of fan assemblies, replacement and/or repair of high voltage sources, extensive clearing of arrays of wires and electrodes that help create air movement, and replacement of filters that clog the devices unless they are cleaned. These devices are often larger, noisier, more complicated, and more expensive than what some users may desire. Often, the location of the device is an issue, as consumers want air cleaning in all rooms of the house. Further, placement within a room is also problematic, as consumers often perceive that stationary air cleaners do not clean the entire airspace of a room and the air in corners of the room would remain stale.

However, even with air purifiers operating in a room, over time airborne contaminants settle upon surfaces. These collections of dust, dander, pollen, and other contaminants are a common problem in dwellings, office spaces, and other work or domestic locations. Such collections of surface contaminants are unpleasant and, on many occasions, may also represent a health problem for many asthmatics and allergy sufferers. Therefore, because air purifiers can only collect contaminates contained in the air, floors and other surfaces on which these contaminates collect must be cleaned periodically to remove them. In most cases, this is carried out manually by sweeping, vacuuming, or dry-mopping. However, such tedious manual activities can be counterproductive, in that cleaning tends to release the surface contaminants as particulates back into the air and thereby increase the concentration of airborne particulate, which in turn decreases ambient air quality.

Robots have long been used as a suitable replacement for manual activity in a number of situations. Recently, robots have being used for practical household cleaning applications. An example of a robot used for autonomous mobile surface treatment is found in U.S. Patent Application Publication No. 2003/0126701; (the '701 application), entitled, "Mobile Robot." The '701 application describes a mobile robot that is capable of autonomous movement across a surface by means of a drive unit that is arranged inside a top-hat-shaped unit. Cleaning devices, such as electrostatic dusters or equipment for vacuuming, can be affixed within the top-hat structure, so that the mobile robot functions as a cleaning robot. One aspect of the invention of the '701 application is to provide a mobile robot which, during a given period of operation, can remove a substantial part of the dust particles that can be found on floor surfaces. However, the robot disclosed in the '701 application does not provide a means of air filtration or other air treatment methods in order to minimize airborne particulates and reduce the overall indoor air contamination.

In comparison, U.S. Patent Application Publication No. 2002/0078830, (the '830 application), entitled, "Air Purifier," describes an intelligent air filtration unit that adapts its operation, based on air quality. When the unit senses that the air quality condition is poor, or is deteriorating, it increases filtration, and when the unit detects that the number of particles per unit volume of air has decreased to a range of acceptable or good air, it automatically reduces filtration. Therefore, the apparatus disclosed in the '830 application provides air filtering as a function of air quality. However, the apparatus of the '830 application does not address surface contaminants and it is not automatically mobile.

In addition to cleaning the air and surfaces of contaminants, another aspect of air purifying or freshening that is of interest to consumers is that of removing odors or providing fragrance to the air. Technology exists to deliver each of these benefits separately as well as in a single product form. In practice, unpleasant odors can be removed or can be modified to exist as a more pleasant scent. Odor modification is frequently accompanied by the addition of a more agreeable scent. Air fresheners are typical odor modifiers, because they employ volatile fragrance agents for odor control by altering a malodor to a more pleasant character or to an acceptable level. Air fresheners were initially used in bathrooms and kitchens and, consequently, the device shape and design has tended to be more functional than attractive. Air fresheners typically ensure a consistent fragrance refill revenue stream for the device manufacturer. Air fresheners are now used in bedrooms and living rooms, however consumers who wish to use air fresheners in these areas of the home may be reluctant to place an unattractive, functional container in these areas.

Thus, it is desirable to develop an autonomous and mobile floor cleaning mechanism that is easy to operate and removes surface contaminants from surfaces without reintroducing a significant amount of the particulates removed from the surface into the air and, consequently, reduces the required frequency of manual cleaning. Further, as a result of the relationship between airborne particulates and surface contaminants, it is also desirable that both air filtration and surface cleaning be performed in a single device. Additionally, as it is desirable to provide the air with a selectable fragrance, it is also desirable that the autonomously mobile air purifier in combination with a surface cleaner include a fragrance providing mechanism in a single device.

SUMMARY OF THE INVENTION

According to a primary aspect of the present invention, a device is provided that includes an air purifying or freshening mechanism in conjunction with both a surface cleaning mechanism and an air fragrancing mechanism within the device. The device has a unitary housing in which each mechanism is enclosed such that all three functions are provided by a single unit. The device also includes a control system disposed within the device that selectively operates each of the mechanisms as needed or desired. In addition, the control system can be programmed in order to operate the various mechanism in autonomous manner whereby the mechanism can be selectively operated, or have their mode of operation modified directly by the control system, in response to certain conditions or parameters sensed by the control system. The control system can also selectively operate a motive mechanism for the device, such that the device can move about the room while simultaneously providing the air purifying, surface cleaning, and air fragrancing functions.

According to another aspect of the present invention, the modes of operation for the various air purifying, surface cleaning, and air fragrancing mechanisms in the device have settings which can be modified by a user through the control system in order to enable the various mechanisms to provide varying levels of functionality based on the user input or modified settings. These user settings can be utilized in conjunction with, or can override the default settings of the control system with regard to each mechanism, such that the device including these three mechanisms can have the mode of operation for each mechanism modified as desired for a particular situation.

According to a further aspect of the present invention, the air purifying and surface cleaning mechanisms of the device can selectively operate in conjunction with one another to clean both the air and surfaces contacted by the device, but also to prevent the discharge of additional particulates from the surface into the air, thereby reducing the mount of particulates in the air that must be removed by the air purifier.

According to still another aspect of the present invention, the control system of the device can be configured to enable the control system to sense any of a number of different conditions on the exterior of the device and subsequently move the device to the source of the sensed condition. When arriving at the source of the sensing condition, the control system can operate one or more of the mechanisms within the device to eliminate the sensed condition within the environment in which the device is located.

Numerous other aspects of the features and advantages of the present invention will become apparent from the following detailed description taken together with the drawing figures.

BRIEF DESCRIPTION OF THE DRAWINGS

The drawings illustrate the best mode currently contemplated in practice in the present invention.

In the drawings.

DETAILED DESCRIPTION OF THE INVENTION

Figure 1A:
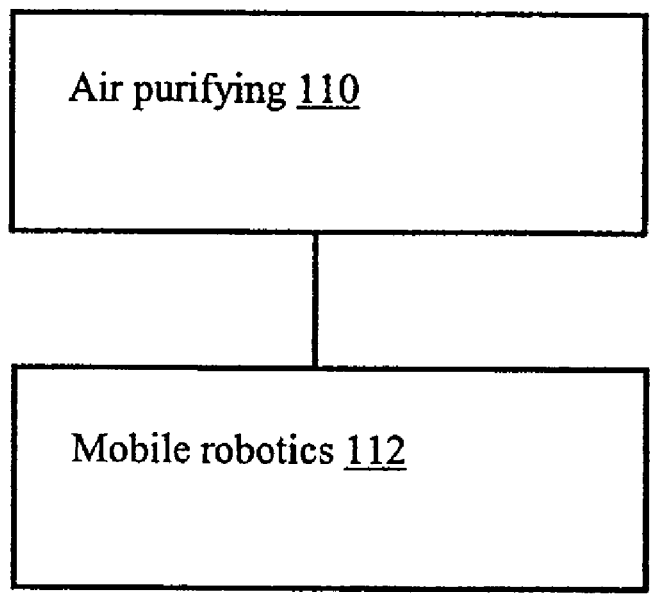
FIG. 1A is a schematic view of an autonomous cleaning device constructed according to the present invention.

With reference now to the drawing figures in which like reference numerals designate like parts throughout the disclosure, FIG. 1A illustrates a functional block diagram of a first embodiment of an autonomously mobile air purifier indicated generally at 100 that is constructed in accordance with the present invention. Autonomously mobile air purifier 100 includes the functional elements of an air purifying mechanism 110 and a mobile robotics mechanism 112.

Air purifying mechanism 110 describes the function of, for example, an air filter mechanism as is known in the art that draws in ambient air that contains contaminants, i.e. smoke, pollen, mold spores, animal dander, and other common particulate, and exhausts air with a reduced level of these impurities. Mobile robotics mechanism 112 provides the autonomous propulsion for autonomously mobile air purifier 100 that is well known to those skilled in the art. For example, mobile robotics mechanism 112 allows a variety of preprogrammed routes to be executed across the floor area of a room (not shown) including, but not limited to, a peripheral loop pattern, a random pattern, a rectilinear pattern that covers all exposed floor space, and a variety of closed-loop patterns, such as figure-eight patterns and the like. Mobile robotics mechanism 112 also allows for independent and adaptive navigation throughout its operation, for example, adaptive route execution that utilizes collision avoidance is commonly used to steer clear of common indoor obstacles such as people, pets and furniture, as is also well known by those skilled in the art. In operation, the autonomously mobile air purifier mechanism 100, transverses a floor under the power of mobile robotics mechanism 112 and provide air purifying by the independent functioning of air purifying mechanism 110.

Figure 1B:
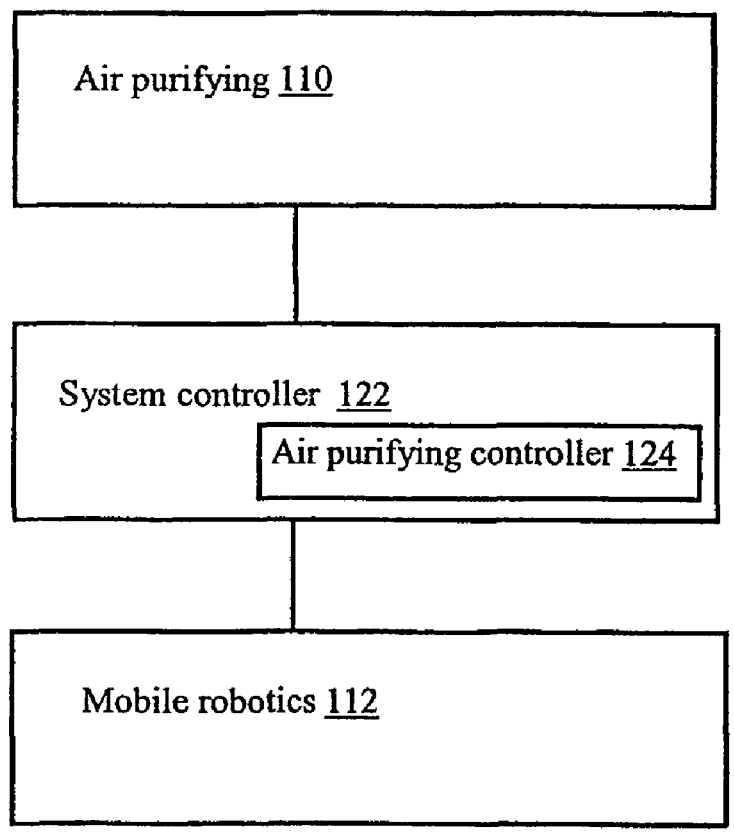
FIG. 1B is a schematic view of a second embodiment of the autonomous cleaning device of the present invention

Referring to FIG. 1B, a functional block diagram is illustrated of a second embodiment of an autonomously mobile air purifier 120 of a more complex configuration. Autonomously mobile air purifier 120 includes the functional elements of air purifying mechanism 110, mobile robotics mechanism 112, and a system controller 122, which further includes an air purifying controller 124.

System controller 122 describes a supervisory processing function that is capable of managing all of the operating functions of autonomously mobile air purifier 120. Air purifying controller 124 describes that function of system controller 122, which is capable of modifying its operation, based on any aspect of the operation of mobile robotics mechanism 112 or the functionality of air purifying mechanism 110. For example, air purifying controller 124 may adapt the air filtration rate of air purifier 120 in response to the speed of autonomously mobile air purifier 120 by monitoring a speed signal (not shown) from mobile robotics mechanism 112 and controlling a fan rate input (not shown) of the air purifying mechanism 110 on air purifier 120.

In operation, the configuration of autonomously mobile air purifier 120, transverses a floor under the power of mobile robotics mechanism 112 and provides air purifying by the action of air purifying mechanism 110 under the control of air purifying controller 124 within system controller 122.

Figure 1C:
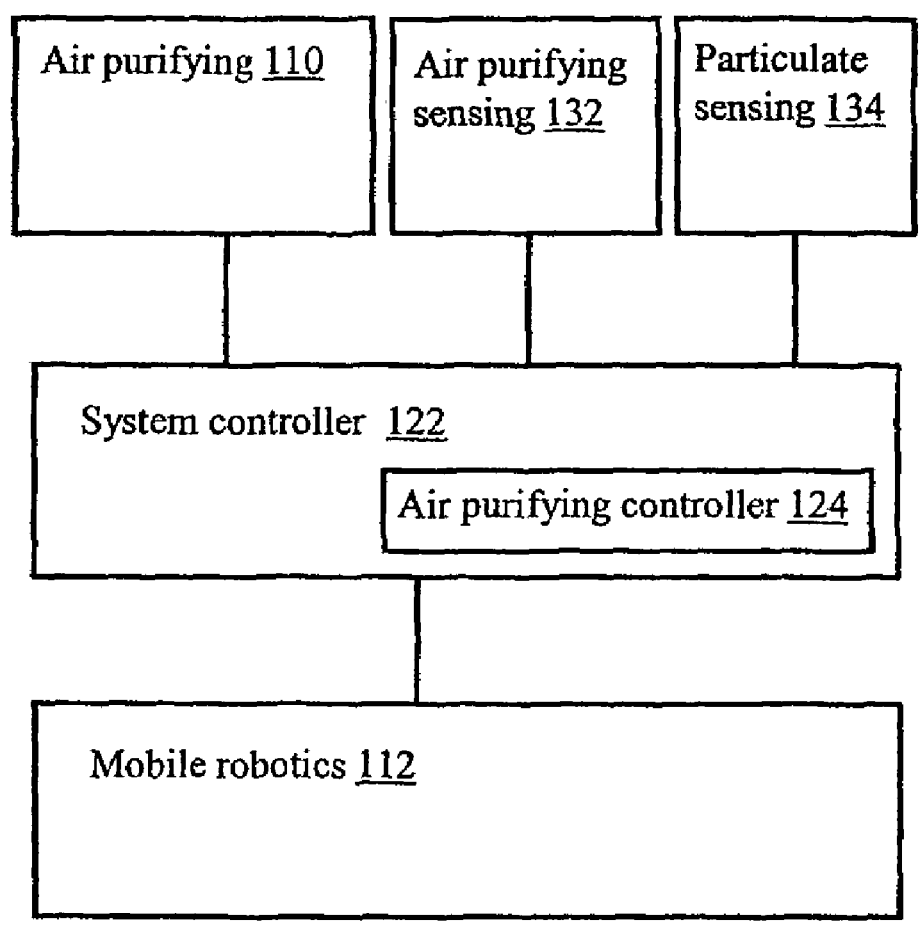
FIG. 1C is a schematic view of a third embodiment of the autonomous cleaning device of the present invention.

FIG. 1C illustrates a functional block diagram of a third embodiment of an autonomously mobile air purifier 130 of a more preferred configuration. Specifically, in addition to including the functional elements of air purifying mechanism 110, mobile robotics mechanism 112, system controller 122, and air purifying controller 124, autonomously mobile air purifier 130 includes an air purifying sensing mechanism 132 and a particulate sensing mechanism 134.

Air purifying sensing mechanism 132 describes the function of monitoring the ability of air purifying mechanism 110 to remove particulates effectively, for example, monitoring the extent of use of an air filter (not shown) in mechanism 110 using suitable sensors (not shown) that are known in the art. Particulate sensing mechanism 134 describes the function of monitoring the degree of particulate concentration in the ambient air of autonomously mobile air purifier 130 by use of a particulate sensor that is well known by those skilled in the art, for example the Model #11026 40CX Plasmacluster Air Purifier, manufactured by Sharp. Air purifying controller 124 describes the specific function of the system controller 122 that is capable of modifying its operation, based on an aspect of mobile robotics mechanism 112 or air purifying mechanism 110, including the information provided by air purifying sensing 132 or particulate sensing mechanism 134. For example, air purifying controller 124 may adapt the air filtration rate of autonomously mobile air purifier 130 by controlling a fan rate input (not shown) of air purifying mechanism 110 in response to the ambient particulate concentration indicated by particulate sensing mechanism 134. Further, air purifying controller 124 may further adapt the air filtration rate of air purifier 130 as a result of the capacity of air purifying mechanism 110 as indicated by air purifying sensing mechanism 132.

In operation, the configuration of autonomously mobile air purifier 130, transverses a floor under the power of mobile robotics mechanism 112 and provides air purifying by the action of air purifying mechanism 110 under the control of air purifying controller 124 within system controller 122 by use of the processed signals (not shown) of air purifying sensing mechanism 132 and particulate sensing mechanism 134.

Figure 2:
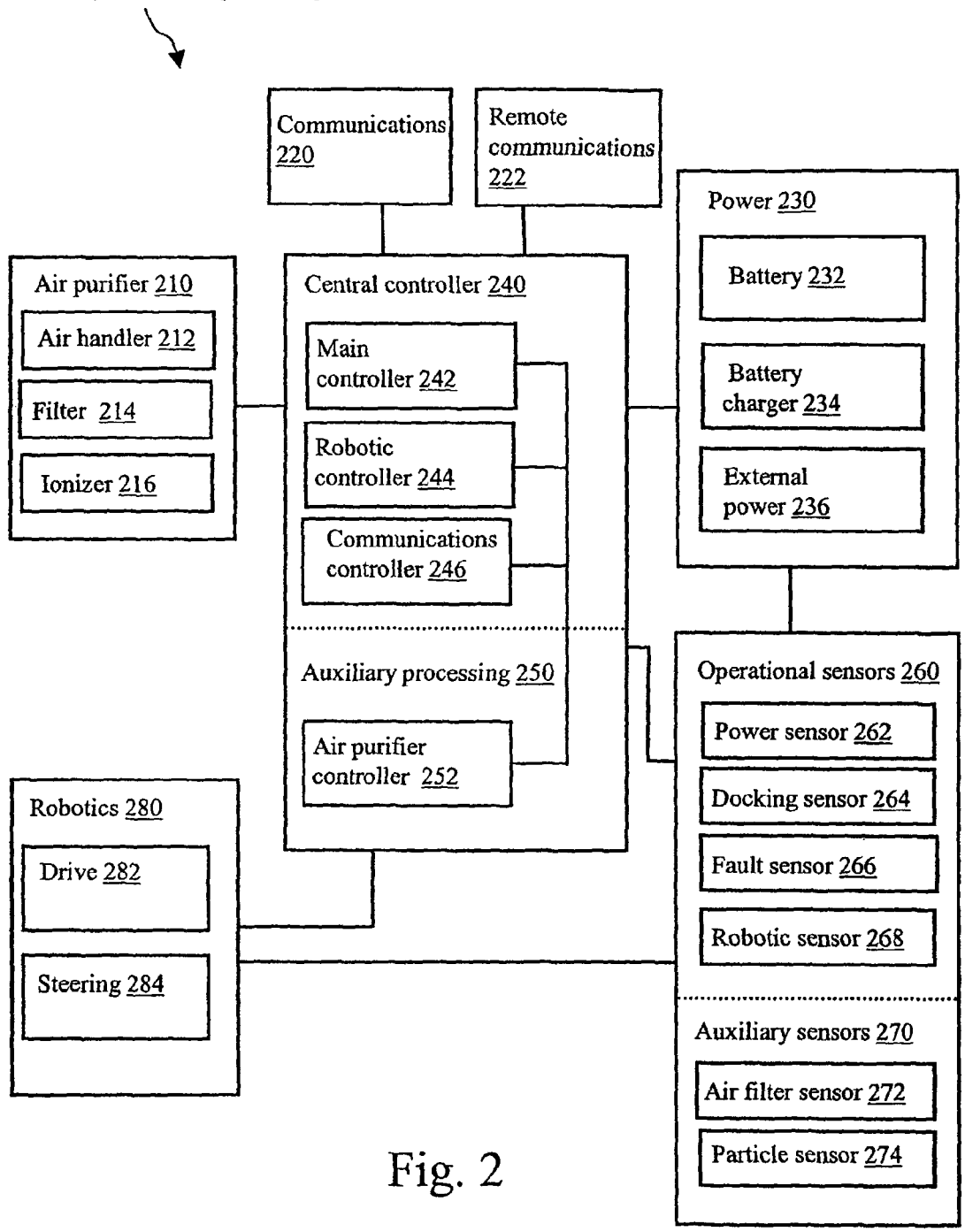
FIG. 2 is a schematic view of a fourth embodiment of the autonomous cleaning device of the present invention.

Referring now to FIG. 2, a block diagram of a fourth embodiment of an autonomously mobile air purifier system 200 is illustrated that depicts the organization of system components of an especially preferred configuration of autonomously mobile air purifier 100. Autonomously mobile air purifier system 200 includes an air purifier mechanism 210 that further includes an air handler 212, a filter 214, and an ionizer 216. Autonomously mobile air purifier system 200 also includes communications input or interface 220, a remote communications input or interface 222, and power source 230 that further includes one or more of a re-chargeable battery 232, a battery charger 234, and a source of external power 236. Autonomously mobile air purifier system 200 also includes a central controller 240, which further contains a main controller 242, a robotic controller 244, and a communications controller 246, and auxiliary processing 250, which further includes air purifying controller 252. Autonomously mobile air purifier system 200 also includes operational sensors 260 and auxiliary sensors 270. Operational sensors 260 further include a power sensor 262, a docking sensor 264, a fault sensor 266, and a robotic sensor 268. Auxiliary sensors 270 include an air filter sensor 272 and a particle and/or odor sensor 274. Finally, autonomously mobile air purifier system 200 includes robotics mechanism 280, which further includes a drive mechanism 282 and a steering or guidance system 284.

Air purifier mechanism 210 provides all the air purification and modification for autonomously mobile air purifier system 200. Air handler 212 further includes the fan, fan motor, air ducts, baffles, air intakes, and exhaust (not shown in FIG. 2) necessary to move and channel the ambient air within autonomously mobile air purifier system 200. Air purifier mechanism 210 also includes filter 214, which provides air cleaning, as is well known to those skilled in the art. Finally, ionizer 216 provides a means to artificially charge particulate that resides within the incoming air steam. The charge (generally positive) is selectively produced by high tension electrodes to be opposite of the natural or induced filter charge (generally negative). The opposing charges enhance the collection of particulate on the filter media thereby providing more effective air purification.

Communications input 220 and remote communications input 222 are the user interfaces for autonomously mobile air purifier system 200 through which an operating mode is selected, for example, an air purification mode in combination with a route to be executed across a floor. Communications input 220 is a local communications means, for example, a display and keypad attached to autonomously mobile air purifier system 200. Remote communications input 222 provides a means of communication from a distance, for example, by wireless or radio control. Communications input 220 and remote communications input 222 also provide status data for autonomously mobile air purifier system 200 to be presented to the user.

Power source 230 is the power source for all functions of autonomously mobile air purifier system 200, and may include, for example, a re-chargeable battery 232, a battery charger 234, and a source of external power 236 that further includes a retractable standard AC power cord (not shown).

Central controller 240 is the central processing unit (CPU) for autonomously mobile air purifier system 200 and is a standard computer and robotic system design that is well known to those skilled in the art. Main controller 242 provides operational control for the overall system functionality, for example, the software operating system, of autonomously mobile air purifier system 200. Robotic controller 244 controls the operation of robotics 280. Communication controller 246 controls the functioning of communications input 220 and remote communications input 222. Auxiliary processing 250 controls the operation of all processing functions not included in central controller 240, for example air purification control. Air purifying controller 252 within auxiliary processing 250 handles the operation of air purifier mechanism 210. The physical components used as the central controller 240 and auxiliary processing 250 may include, for example, a microprocessor such as that incorporated in automated consumer products (e.g., Roomba Vacuum Cleaners), memory such as Random Access Memory (RAM), "Flash" programmable read-only memory, and other associated digital logic such as latches, buffers, glue logic, and the like.

Robotics mechanism 280 provides a mechanical means of propulsion and steering for autonomously mobile air purifier system 200. Drive mechanism 282 contains components such as motors, gear mechanisms, sensing modules, transmitting/receiving centers, connecting hardware, wheels, guide surfaces, and brakes (as needed for propelling autonomously mobile air purifier system 200 forward and reverse, or to stop the unit). The action of starting/stopping can also be aided by peripheral logic to provide intermittent motion. Self-propelled movement of the purifier system 200 is determined by a guidance system 284 that provides a means for momentary, self-diagnostic or pre-set changes in direction of autonomously mobile air purifier system 200.

Operating intelligence 260 relies on various sensors that report operation status for a variety of support functions to central controller 240. Power sensor 262 monitors battery life, docking sensor 264 is used to detect a docking station 1300 for battery recharging (shown in FIG. 13). Fault sensor 266 determines when autonomous air and surface cleaning system 200 has become overstressed because of impact, a fall, a stalled condition or exposure to an unfriendly environment, i.e., water and oil. Robotic sensor 268 detects these types of conditions using technologies such as ultrasonic or IR technology, as is well known by those skilled in the art, which react to various stimuli in the environment that are necessary for robotic control, for example, the presence of an obstruction in the path of autonomously mobile air purifier system 200. Auxiliary sensors 270 provide feedback for the air purification mechanisms of autonomously mobile air purifier system 200. Air filter sensor 272, for example, senses air filter quality, i.e. when the air flow downstream of a conventional filter structure is significantly reduced from its original state to determine that the filter is fully consumed. Alternatively, to or in conjunction with air filter sensor 272, filter technologies that precipitate rather than trap particulate may rely on particle sensor 274 to detect the concentration of downstream airborne particulate that has escaped the filter signaling that filter capacity is approaching, or reached, or exceeded, such that the filter needs to be replaced.

In operation, autonomously mobile air purifier system 200 performs the following functions in an autonomous manner: 1) status monitoring; 2) operator input monitoring; 3) robotics control; and 4) air purification control.

In performing the status monitoring function, central controller 240 periodically reads status from operational sensors 260 to determine the operational health, and to monitor the normal functioning of autonomously mobile air purifier system 200. For example, the parameters monitored by central controller 240 include, but are not limited to, the remaining charge on battery 232, which is read by power sensor 262, the degree of air filter usage within filter 214, which is read by air filter sensor 272, a fault, i.e., shock, to autonomously mobile air purifier system 200, caused by, for example dropping, which is read by fault sensor 266, and obstacles in the path of autonomously mobile air purifier system 200, for example, furniture, a person, or a pet, which are detected by robotic sensor 268, among others. Central controller 240 continuously monitors status when conditions indicate that user intervention is required, for example, to replace air filter 214, at which point central controller 240 produces the appropriate message (not shown), for example "check air filter," by using communications input 220 or remote communications input 222, in order to indicate a requested user action.

To perform the operator input monitoring function, when a user enters a mode command on communications input 220 or remote communications input 222, central controller 240 receives an interrupt, suspends its current operation, reads the user's desired mode change, and takes the appropriate action. For example, when a command to change fan speed is received from an input 220 or 222, central controller 240 responds by sending control signals to air purifier mechanism 210 to select the desired fan speed within air handler mechanism 212.

In performing the robotics control function, when a user enters a drive mode command on communications interface 220 or remote communications input 222, central controller 240 reads the user's desired mode change and takes the appropriate action. For example, if "random pattern" surface cleaning mode is initiated, robotic controller 244 within central controller mechanism 240 executes a drive control algorithm and sends a control signal back to robotics mechanism 280, including drive mechanism 282 and steering mechanism 284, to maintain the proper path, speed, direction of autonomously mobile air purifier system 200, according to the feedback given by robotic sensor 268. The system drive control algorithm is an artificial intelligence guidance system known in the art.

To perform the air purification control function, when a user enters an air purification mode command on communications input 220 or remote communications input 222, central controller 240 begins the air purification mode. For example, when a command to change the air purification mode is entered, central controller 240 responds by sending the appropriate control signals to air purifier 210 to select the fan speed within air handler mechanism 212.

Figure 3:
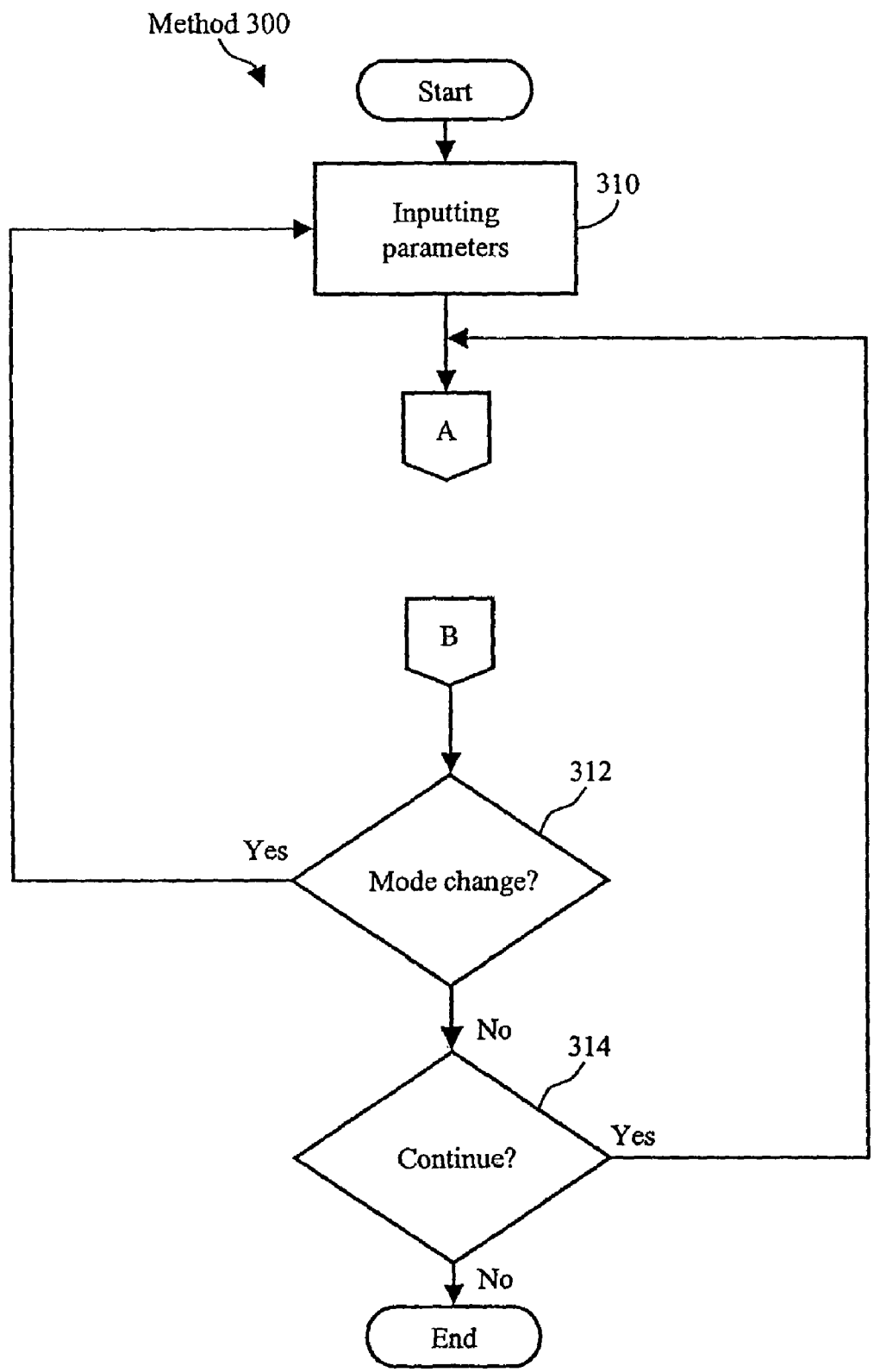
FIG. 3 is a flow chart illustrating the overall method of operation of the autonomous cleaning device of FIG. 2.

FIG. 3 is a flow diagram of a method 300 of inputting parameters into autonomously mobile air purifier system 200 regarding the overall functioning of the system 200. The method 300 includes the following steps:

Step 310: Inputting Parameters

In this step, after starting the system 200, a user enters a mode command on communications input 220 or remote communications input 222, after which central controller 240 receives an interrupt, suspends its current operation, reads the user's desired mode change, and executes method 400 (FIG. 4) and/or method 700 (FIG. 7), and/or method 1000 (FIG. 10) concerning the different functions of the system 200 at the beginning and end of which are represented by blocks A and B in FIG. 3, in a manner to be described. Method 300 then proceeds from step 310 to step 312.

Step 312: Mode Change?

In this decision step, central controller 240 determines whether a mode change is required based upon the input parameters and the results of the particular executed method 400, 700 or 1000. If mode change is required, method 300 returns to step 310 to receive the parameters for the mode change. If no change in mode of a portion for the system 200 is required, method 300 proceeds from step 312 to step 314.

Step 314: Continue?

In this decision step, central controller 240 determines whether a command has been received from communications input 220 or remote communications input 222 to continue operation of the system 200 in the selected mode. If yes, method 300 executes method 400, 700 or 1000 and proceeds to step 312; if no, method 300 ends.

Figure 4:
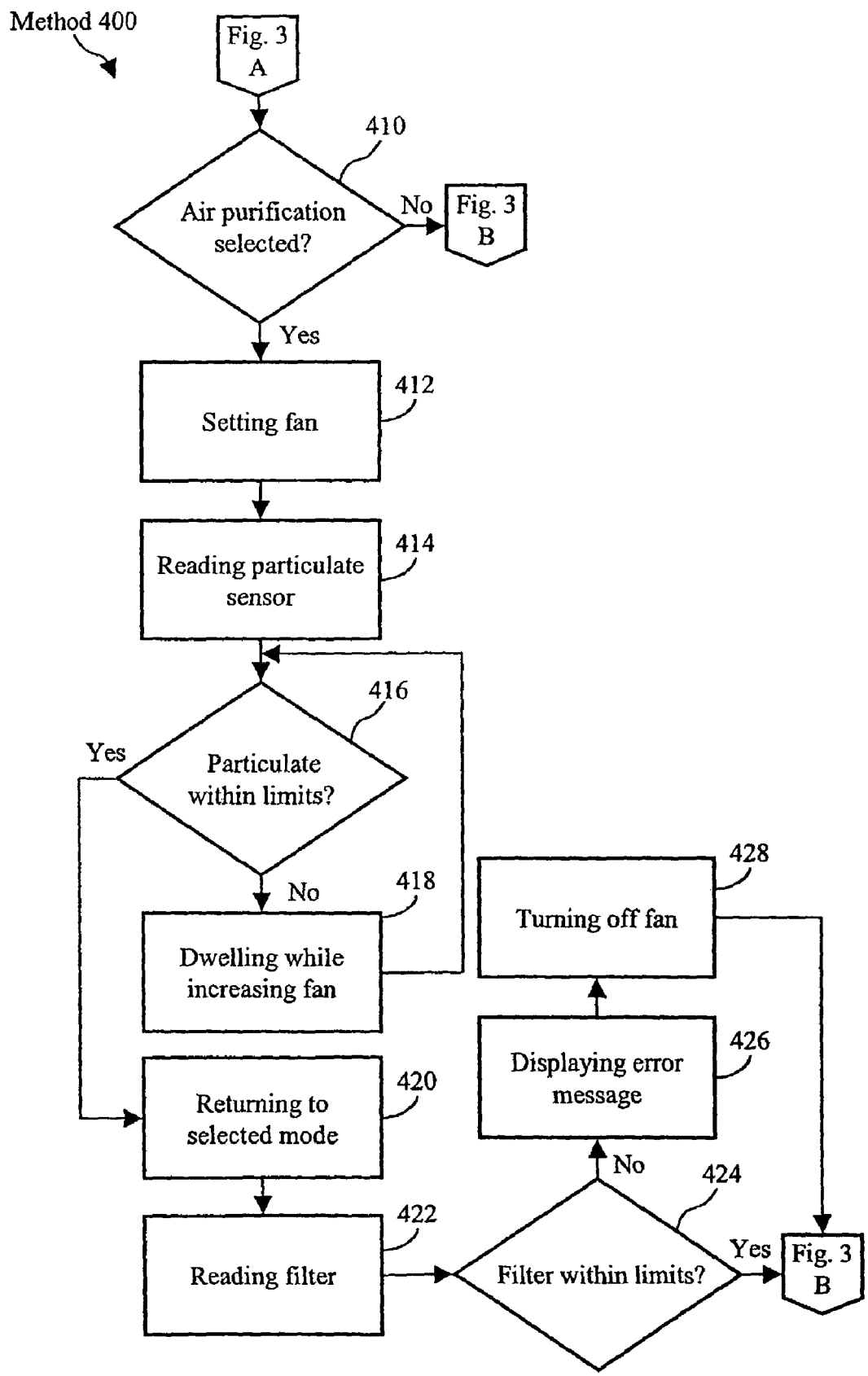
FIG. 4 is a flow chart illustrating the method of operation of the air purification mechanism of the autonomous cleaning device of FIG. 2.

FIG. 4 is a flow diagram of a method 400 of enabling or activating the air purification function for autonomously mobile air purifier system 200 that is utilized in the method 300 and indicated in FIG. 3 by blocks A and B. The method 400 includes the following steps.

Step 410: Air Purification Selected?

In this decision step, which is also block A in method 300, central controller 240 determines whether air purification has been selected by a user input 220 or 222. If yes, method 400 proceeds to step 412, but if no, method 400 returns to method 300 (block B) and proceeds as described previously regarding method 300.

Step 412: Setting Fan

In this step, air purifier controller 252 receives an interrupt, suspends its current operation, reads the user's desired fan speed input, and sends a control signal to air handler mechanism 212, which modifies fan speed in response to the user input. Method 400 then proceeds to step 414.

Step 414: Reading Particulate Sensor

In this step, air purifier controller 252 reads particulate sensor 274. Method 400 then proceeds to step 416.

Step 416: Particulate Within Limits?

In this decision step, air purifier controller 252 determines whether the particle reading in step 414 is within predetermined or user-selected limits for the operation of the system 200. If yes, method 400 proceeds to step 420, but if no, method 400 then proceeds to step 418.

Step 418: Dwelling While Increasing Fan

In this step, air purifier controller 252 communicates a high ambient particulate level to main controller 242, which determines the most appropriate response, based on the current operation mode and the other environmental conditions for the system 200. For example, main controller 242 can instruct robotics mechanism 280 to cause autonomously mobile air purifier system 200 to dwell in the location of sensed high level of ambient particulates, while simultaneously commanding air purifier controller 252 to increase fan rate within air handler mechanism 212. Method 400 then returns to step 416 to sense the particulate level around the system 200. This loop continues until the sensed particulate level is below the limit defined in the system 200, when the method then moves to step 420.

Step 420: Returning to Selected Mode

In this step, main controller 242 commands air purifier controller 252 to return to the user selected mode. For example, main controller 242 instructs robotics mechanism 280 to cause autonomously mobile air purifier system 200 to initiate a random movement, while commanding air purifier controller 252 to decrease the fan rate within air handler mechanism 212. Method 400 then proceeds to step 422.

Step 422: Reading Filter

In this step, air purifier controller 252 reads air filter sensor 272. Method 400 then proceeds to step 424.

Step 424 Filter Within Limits?

In this decision step, air purifier controller 252 determines whether the status of filter 214 that was read in step 414 is within proper predetermined or user-defined limits. If yes, method 400 moves to block B in method 300 and proceeds as described previously concerning method 300. However, if the status of filter 214 received by sensor 272 is not within the specified limits, then method 400 proceeds to step 426.

Step 426: Displaying Error Message

In this step, air purifying controller 248 communicates the status of filter 214 to main controller 242, which instructs robotics controller 244 to display an error message on communications input 220 and/or remote input 222. Method 400 then proceeds to step 428.

Step 428: Turning Off Fan

In this step, air purifier controller 252 communicates the status of filter 214 to main controller 242, which determines the most appropriate response, based on the current operation mode and the other environmental conditions. For example, main controller 242 instructs air purifier controller 252 to turn off the fan within air handler mechanism 212. Method 400 then returns to block B in method 300 and proceeds as prescribed previously regarding method 300.

Figure 5A:
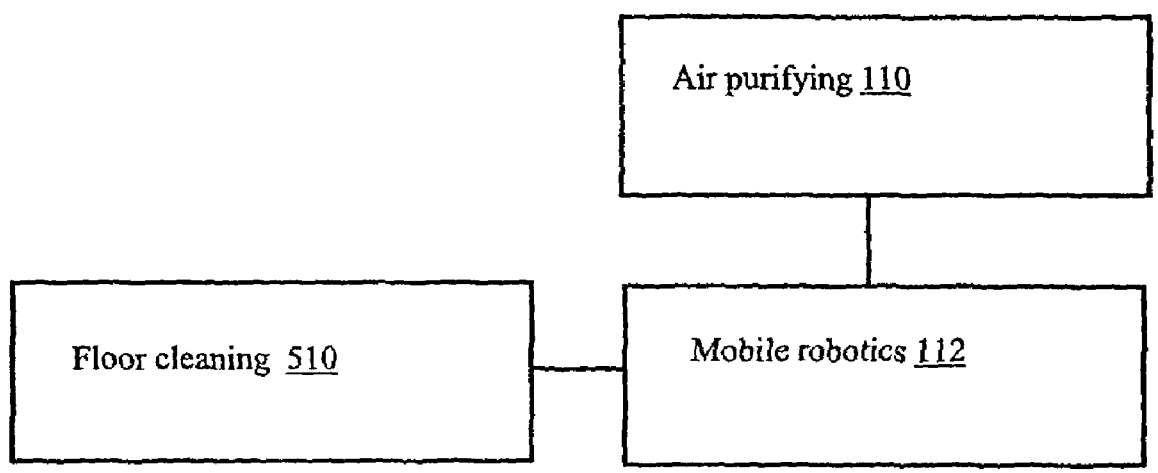
FIG. 5A is a schematic view of a fifth embodiment of the autonomous cleaning device of the present invention.

Referring now to FIG. 5A, a functional block diagram of a fifth embodiment of an autonomously mobile air purifier and surface cleaner 500 is shown. Autonomously mobile air purifier and surface cleaner 500 includes the functional elements of air purifying mechanism 110, mobile robotics mechanism 112 and a floor cleaning mechanism 510.

Floor cleaning mechanism 510 describes the function of, for example, a cleaning mechanism that removes particulate that accumulates on the floor from a variety of sources. This includes small airborne contaminates that are not trapped by normal air filtration, i.e., dust, pollen, mold spores, allergens as well as larger forms of particulate that are deposited by pets and people, i.e., dander, crumbs and dirt. This range of contaminates are removed from the floor surface by mechanical means (wet or dry), electronic applications (charged and discharged) and combinations thereof and disposed of within autonomously mobile air purifier and surface cleaner 500, with minimal dispersal into the ambient air.

In operation, the simplest configuration of autonomously mobile air purifier and surface cleaner 500, transverses a floor under the power of mobile robotics mechanism 112, provides air purifying by the independent functioning of air purifying mechanism 110, and provides floor cleaning by the independent functioning of floor cleaning mechanism 510.

Figure 5B:
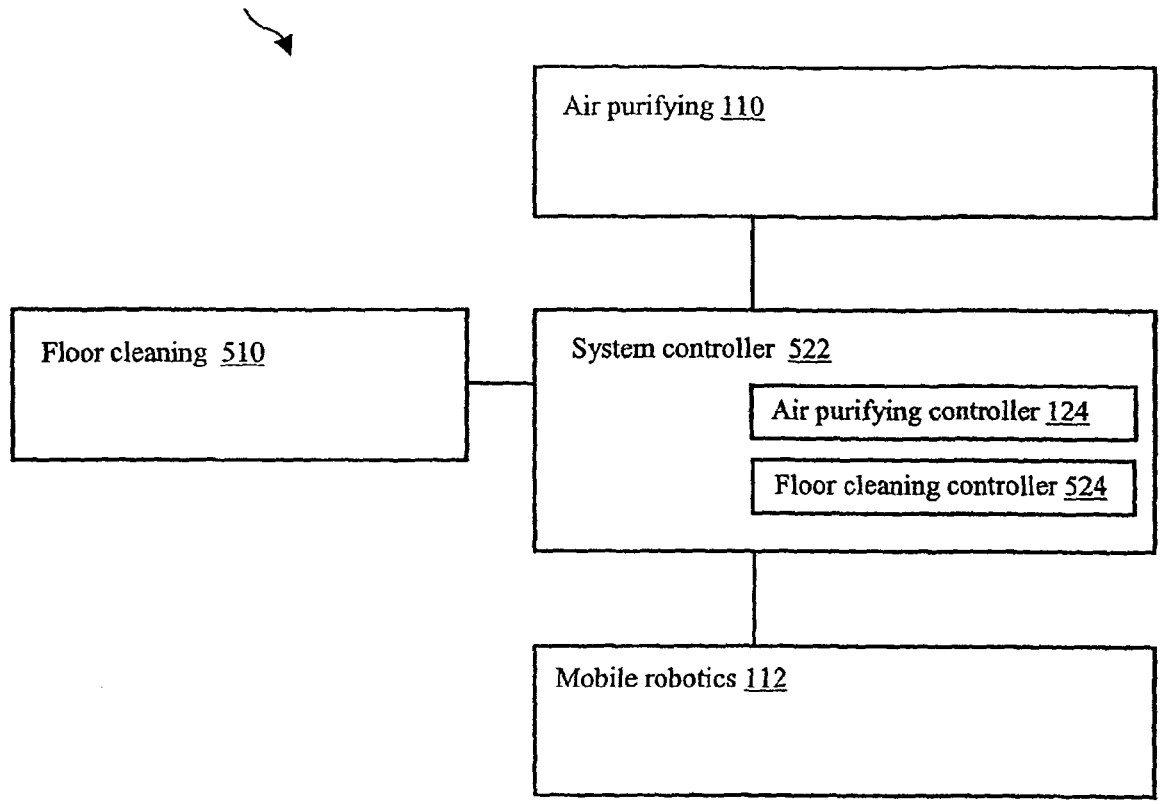
FIG. 5B is a schematic view of a sixth embodiment of the autonomous cleaning device of the present invention.

FIG. 5B illustrates a functional block diagram of a sixth embodiment of an autonomously mobile air purifier and surface cleaner 520. Autonomously mobile air purifier and surface cleaner 520 includes the functional elements of air purifying mechanism 110, mobile robotics mechanism 112 and floor cleaning mechanism 510, and a system controller 522, which further includes an air purifying controller 124 and a floor cleaning controller 524.

System controller 522 describes a supervisory processing function that is capable of managing the operation of autonomously mobile air purifier and surface cleaner 520. Floor cleaning controller 524 describes that function of system controller 522 that is capable of modifying its operation, based on any aspect of the operation of mobile robotics mechanism 112 or the functionality of air purifying mechanism 110 or the functionality of floor cleaning mechanism 510. For example, floor cleaning controller 524 may adapt the rate of deployment of a floor cleaning medium (not shown) in response to the speed of autonomously mobile air purifier and surface cleaner 520.

In operation, the configuration of autonomously mobile air purifier and surface cleaner 520, illustrated in FIG. 5B, transverses a floor (not shown) under the power of mobile robotics mechanism 112 and provides air purifying by the action of air purifying mechanism 110, under the control of air purifying controller 124, and surface cleaning under the control of floor cleaning controller 524 within system controller 522.

Figure 5C:
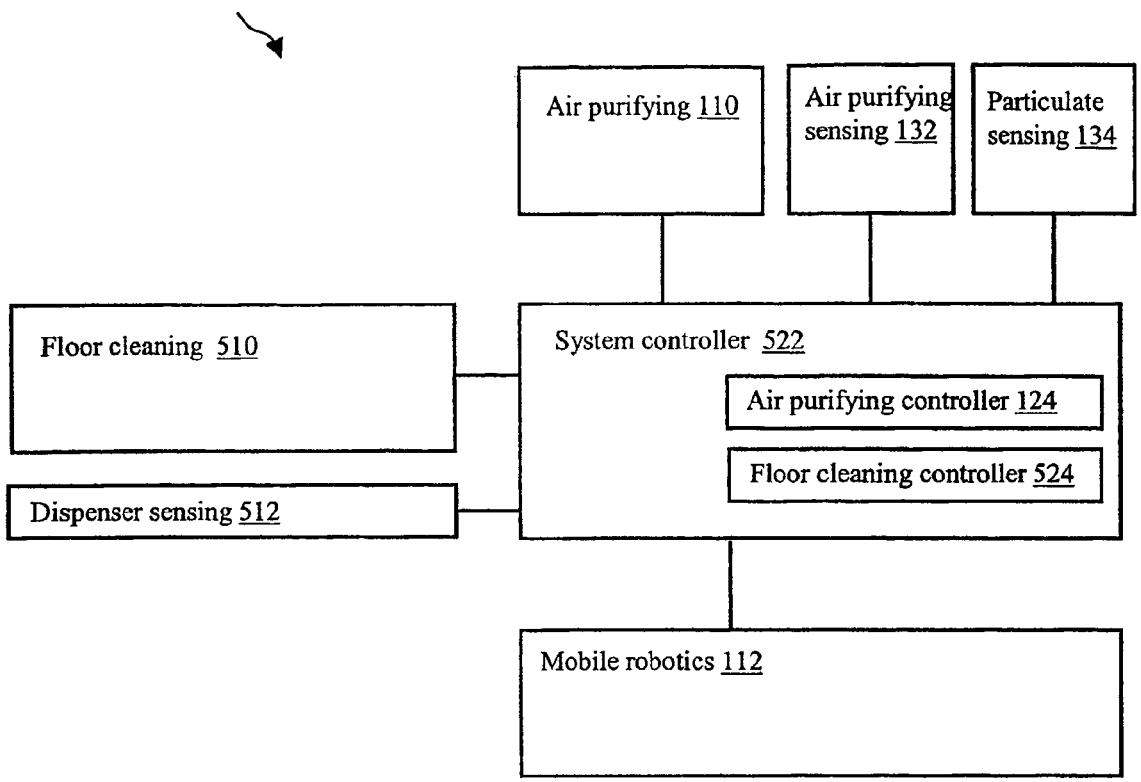
FIG. 5C is a schematic view of a seventh embodiment of the autonomous cleaning device of the present invention.

Looking now at FIG. 5C, a functional block diagram or seventh embodiment of an autonomously mobile air purifier and surface cleaner 530 is illustrated. Autonomously mobile air purifier and surface cleaner 530 includes the functional elements of air purifying mechanism 110, air purifying sensing mechanism 132 and particulate sensing mechanism 134, floor cleaning mechanism 510, dispenser sensing mechanism 512, mobile robotics mechanism 112, and system controller mechanism 522, which further includes air purifying controller 124 and floor cleaning controller 524.

Dispenser sensing mechanism 512 describes the function of monitoring the extent of usage of a floor cleaning medium or element (e.g., 1510 in FIG. 15) to determine whether it has been expended. Floor cleaning controller 524 within system controller 522 describes that function of system controller 122 that is capable of modifying its operation, based on any aspect of mobile robotics mechanism 112, air purifying mechanism 110, or floor cleaning mechanism 510, including the information provided by air purifying sensing mechanism 132, particulate sensing mechanism 134 or dispensing sensing mechanism 512. For example, floor cleaning controller 524 may adapt the rate of deployment of the floor cleaning medium as a function of the capacity of floor cleaning mechanism 510, as indicated by dispenser sensing mechanism 512.

In operation, the configuration of autonomously mobile air purifier and surface cleaner 530, transverses a floor under the power of mobile robotics mechanism 112 and provides air purifying by the action of air purifying mechanism 110, under the control of air purifying controller 124, and surface cleaning by floor cleaning mechanism 510 under the control of floor cleaning controller 524 within system controller 522 by use of the processed signals (not shown) of air purifying sensing mechanism 132, particulate sensing mechanism 134, and dispenser sensing mechanism 512.

Figure 6:
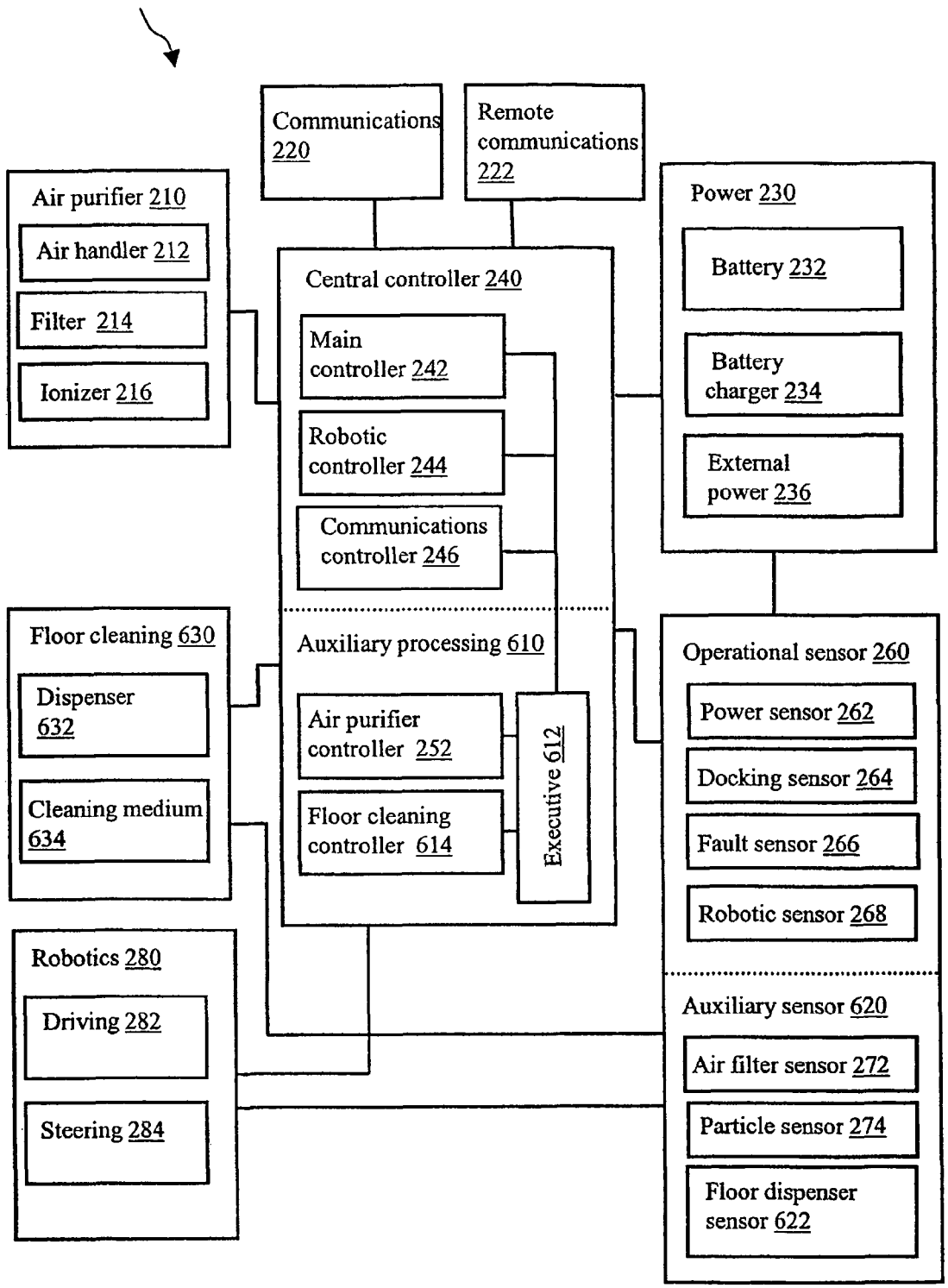
FIG. 6 is a schematic view of an eighth embodiment of the autonomous cleaning device of the present invention.

Looking now at FIG. 6, a system block diagram of an eighth embodiment of an autonomously mobile air purifier and surface cleaner system 600 is shown that depicts the organization of system components in an exemplarity configuration of autonomously mobile air purifier and surface cleaner 530. Autonomously mobile air purifier and surface cleaner system 600 includes air purifier mechanism 210 that further includes air handler 212, filter 214, and ionizer 216. Autonomously mobile air purifier and surface cleaner system 600 also includes communications input or interface 220, remote communications input or interface 222, and power source 230, which can include one or more re-chargeable battery 232, battery charger 234, and external power 236. Autonomously mobile air purifier and surface cleaner system 600 also includes central controller 240, which further contains main controller 242, robotic controller 244, and communications controller 246. Auxiliary processing 610 further includes air purifier controller 252, an executive controller 612, and a floor cleaning controller 614. Autonomously mobile air purifier and surface cleaner system 600 also includes operational sensors 260, which further include power sensor 262, docking sensor 264, fault sensor 266, and robotic sensor 268. Auxiliary sensors 620 include air filter sensor 272, particle sensor 274, and floor dispenser sensor 622. Autonomously mobile air purifier and surface cleaner system 600 also includes robotics mechanism 280, which further include drive mechanism 282 and a steering mechanism or guidance system 284. Finally, autonomously mobile air purifier and surface cleaner system 600 includes floor cleaner mechanism 630, which that further includes dispenser 632 and cleaning medium 634.

Floor cleaning mechanism 630 is the overall mechanical means of removing surface contaminants. Cleaning medium 634 is the means of removal of surface contaminants and includes, for example, a surface that operates in both attractable and releasable modes. This feature could be mechanical (a dry, semi-adhesive material) or electronic (a reversible charged media) that captures particulates as autonomously mobile air purifier and surface cleaner system 600 traverses a floor. Such means for managing the removal of particulate can be found in simple hand-held products for lint-removal or with more sophisticated applications as developed for the manufacture of fabric, polymer film and non-woven media and related products. Dispenser 632 is the mechanism that provides cleaning medium 634. Auxiliary sensors 620 provide feedback for the air purification mechanisms and floor cleaning mechanisms of autonomously mobile air purifier and surface cleaner system 600. Floor dispenser sensor 622 within auxiliary sensors 620 provides feedback that indicates the extent of usage of cleaning medium 634 used within floor cleaning mechanism 630 to determine whether it has been expended. Executive controller 612 within auxiliary processing 250 provides the supervisory control between air purifier controller 252 and floor cleaning controller 614. Floor cleaning controller 614 handles the oversight and the control functions that coordinate the activities necessary for surface cleaning, i.e., coordinating the deployment of cleaning medium 634 in concert with dispenser 632, as monitored by floor dispensing sensor 622, within the context of the other processes of autonomously mobile air purifier and surface cleaner system 600.

In operation, autonomously mobile air purifier and surface cleaner system 600 performs the following functions in an autonomous manner: 1) status monitoring; 2) operator input monitoring; 3) robotics control; 4) air purification; and 5) floor surface cleaning, among others. In addition to the functionality listed above and previously described with regard to FIG. 2, the further functional elements of FIG. 6 are described in operation as follows.

In performing the surface cleaning control function, when a user enters surface cleaning mode command on communications interface 220 or remote communications interface 222, central controller 240 commences the air purification mode. For example, when a command to change the surface mode is entered, central controller 240 responds by sending the appropriate control signals to executive controller 612 and floor cleaning controller 614, which engages floor cleaning mechanism 630 by causing dispenser 632 to deploy cleaning medium 634.

Figure 7:
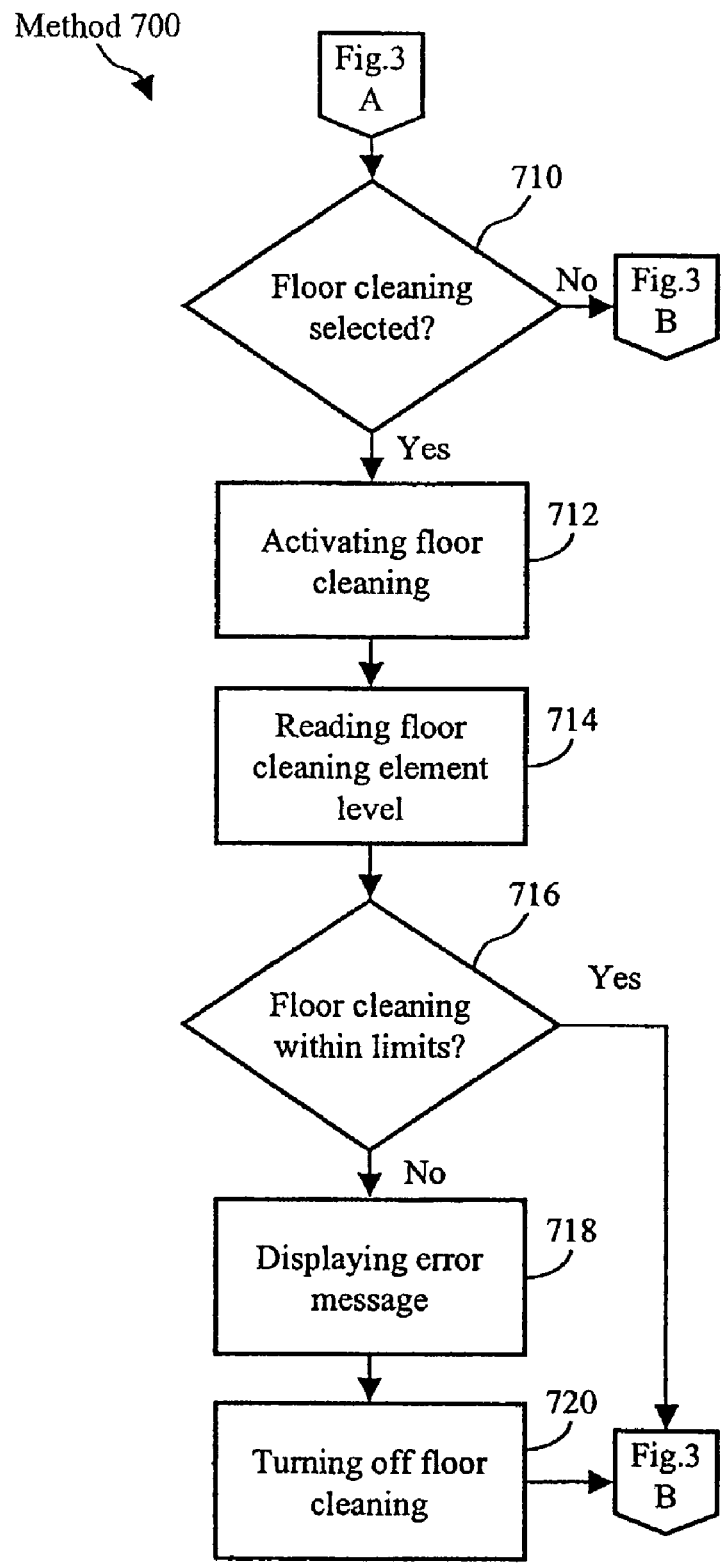
FIG. 7 is a flow chart illustrating the method of operation of the floor cleaning mechanism of the autonomous cleaning device of FIG. 6.

Looking now at FIG. 7, a flow diagram of a method 700 of enabling or activating the surface cleaning function for autonomously mobile air purifier and surface cleaner system 600 is illustrated that is employed in conjunction with the method 300 and indicated in FIG. 3 by blocks A and B. Method 700 includes the following steps.

Step 710: Floor Cleaning Selected?

In this decision step, which is represented by block A in method 300 in FIG. 3, central controller 240 determines whether floor cleaning has been selected by an input from the user, such as through communication input 220 or remote input 222. If yes, method 700 proceeds to step 712, but if no, method 700 returns to method 300 and proceeds in the manner described previously regarding method 300.

Step 712: Activating Floor Cleaning

In this step, main controller 242 receives an interrupt, suspends its current operation, and sends a control signal to executive 612, which in turn instructs floor cleaning controller 614 to engage floor cleaning mechanism 630, which thereby causes dispensing mechanism 632 to distribute cleaning medium 634. Method 700 then proceeds to step 714.

Step 714: Reading Floor Cleaning Element Level

In this step, floor cleaning controller 614 reads a signal received from floor dispenser sensor 622 to determine the level or status of cleaning medium 834. Method 700 then proceeds to step 716.

Step 716 Cleaning Medium Within Limits?

In this decision step, floor cleaning controller 612 determines whether the status of cleaning medium 634 that was read in step 714 is within proper predetermined or user-input limits. If yes, method 700 then moves to block B in method 300 and proceeds as described previously concerning method 300. However, if the status of the cleaning medium 834 determined by the sensor 622 is outside these limits, method 700 proceeds to step 718.

Step 718: Displaying Error Message

In this step, floor cleaning controller 614 communicates the status of cleaning medium 634 to main controller 242 via executive controller 612, which instructs communications controller 246 to display an error message on communications interface 220 or remote interface 222. Method 700 then proceeds to step 720.

Step 720: Turning Off Floor Cleaning

In this step, floor cleaning controller 614 communicates the status of cleaning medium 634 to main controller 242 via executive controller 612, which determines the most appropriate response, based on the current operation mode and the other environmental conditions of the system 600. For example, main controller 242 instructs floor cleaning controller 614 to suspend the operation of dispenser 632. Method 700 then returns to block B in method 300 and proceeds in the manner described previously regarding method 300.

Figure 8A:
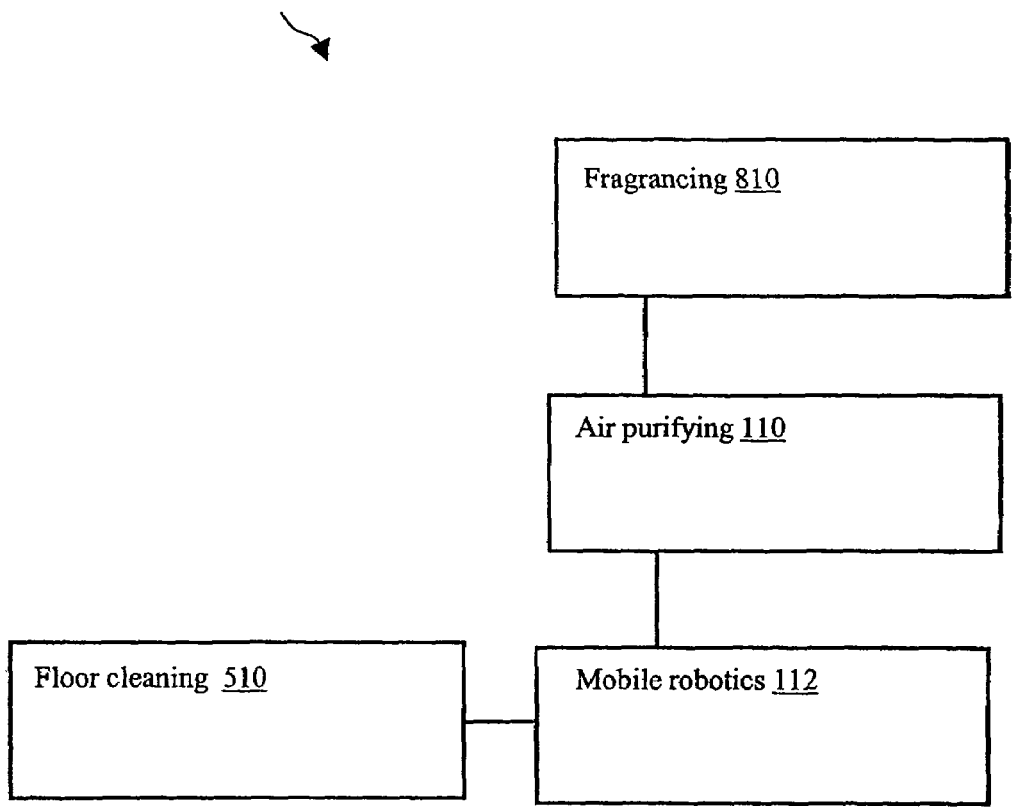
FIG. 8A is a schematic view of a ninth embodiment of an autonomous cleaning device of the present invention.

FIG. 8A illustrates a functional block diagram of an ninth embodiment of an autonomously mobile air and surface cleaner and fragrancer 800. Autonomously mobile air and surface cleaner and fragrancer 800 includes the functional elements of air purifying mechanism 110, mobile robotics mechanism 112, and floor cleaning mechanism 510 and fragrancing mechanism 810.

Fragrancing mechanism 810 describes the function of a device that imparts an aroma into the surrounding air, for example, by use of a mechanism that allows one or more selected fragrant oils to be evaporated and delivered into the ambient air through air handler 212.

In operation, the simplest configuration of autonomously mobile air and surface cleaner and fragrancer 800, transverses a floor under the power of mobile robotics mechanism 112 and provides air purifying by the independent functioning of air purifying mechanism 110, floor cleaning by the independent functioning of floor cleaning mechanism 510, and fragrancing by the independent functioning of fragrancing mechanism 810.

Figure 8B:
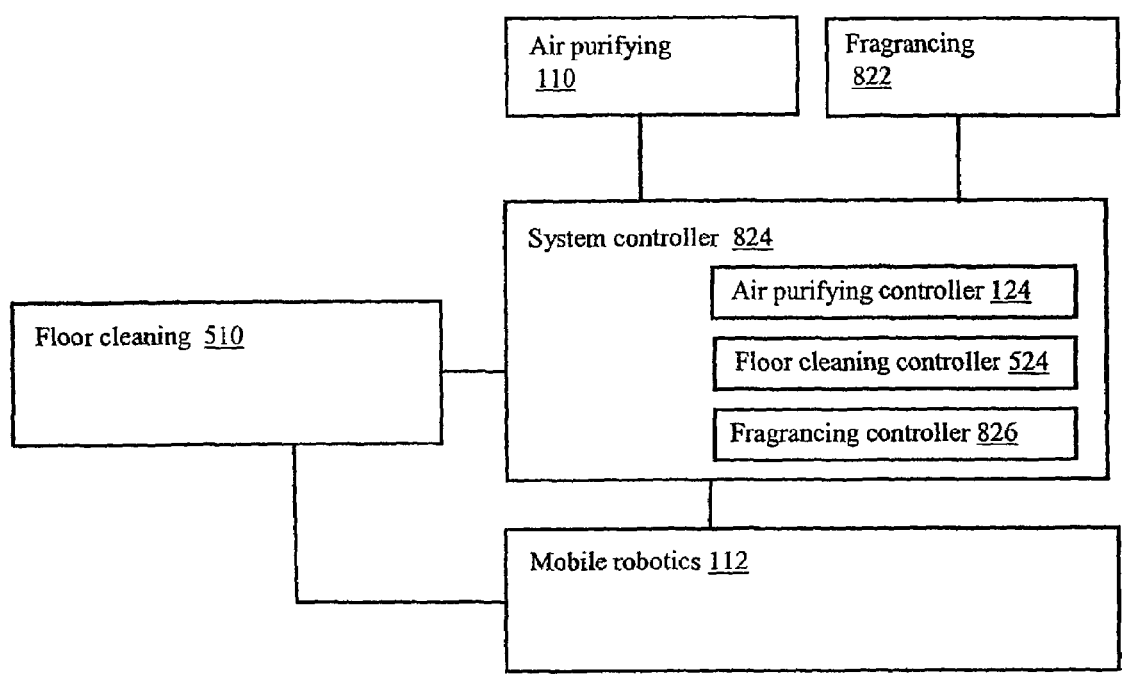
FIG. 8B is a schematic view of a tenth embodiment of the autonomous cleaning device of the present invention.

Referring to FIG. 8B, a functional block diagram of a tenth embodiment of an autonomously mobile air and surface cleaner and fragrancer 820 is shown. Autonomously mobile air and surface cleaner and fragrancer 820 includes the functional elements of air purifying mechanism 110, mobile robotics mechanism 112, and floor cleaning mechanism 510 and a fragrancing mechanism 822, and a system controller 824, which further includes air purifying controller 124, floor cleaning controller 524, and fragrancing controller 826.

System controller 824 describes a supervisory processing function that is capable of managing the operation of autonomously mobile air and surface cleaner and fragrancer 820. Fragrancing controller 826 describes that function of system controller 824 that is capable of modifying its operation, based on any aspect of the operation of mobile robotics mechanism 112, the functionality of air purifying mechanism 110, the functionality of floor cleaning mechanism 510, or the functionality of fragrancing mechanism 822. For example, fragrancing controller 826 may adapt the concentration of a fragrancing medium (not shown) in response to the speed of autonomously mobile air and surface cleaner and fragrancer 820.

In operation, the configuration of autonomously mobile air and surface cleaner and fragrancer 820, transverses a floor under the power of mobile robotics mechanism 112 and provides air purifying by the action of air purifying mechanism 110, under the control of air purifying controller 124, surface cleaning, under the control of floor cleaning controller 522, and fragrance by means of fragrancing mechanism 822, under the control of fragrancing controller 826 within system controller 824.

Figure 8C:
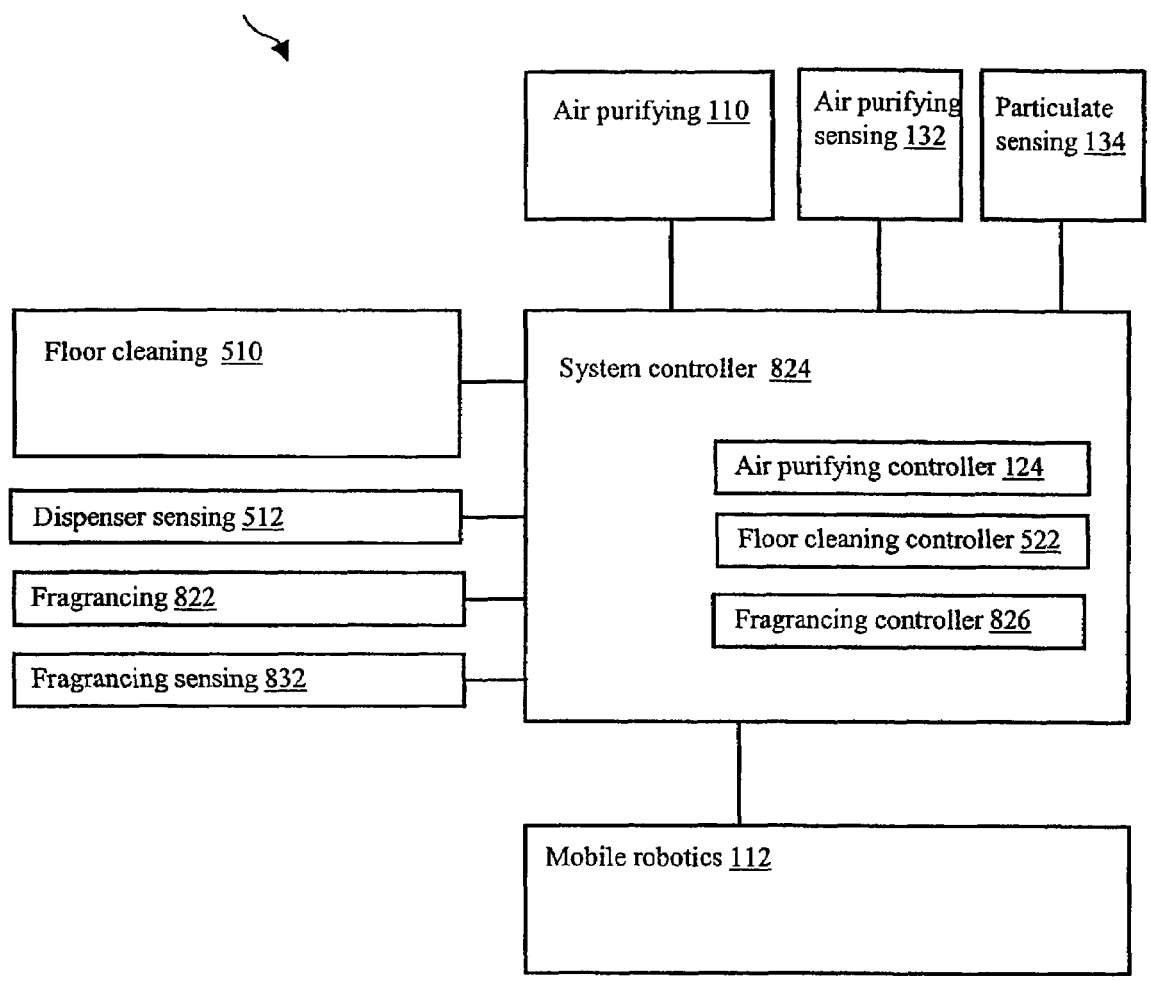
FIG. 8C is a schematic view of an eleventh embodiment of the autonomous cleaning device of the present invention.

Looking now at FIG. 8C, a functional block diagram of an eleventh embodiment of an autonomously mobile air and surface cleaner and fragrancer 830 is illustrated. An autonomously mobile air and surface cleaner and fragrancer 830 includes the functional elements of air purifying mechanism 110, air purifying sensing mechanism 132, particulate sensing mechanism 134, floor cleaning mechanism 510, dispenser sensing mechanism 512, fragrancing mechanism 822, and fragrancing sensing mechanism 832, mobile robotics mechanism 112, and system controller 824, which further includes air purifying controller 124, floor cleaning controller 522, and fragrancing controller 826.

Fragrancing sensing mechanism 832 describes the function of monitoring the extent of usage of a fragrancing element (not shown) to determine whether it has been expended. Fragrancing controller 822 within system controller 824 describes that function of system controller 824 that is capable of modifying its operation, based on any aspect of mobile robotics mechanism 112, air purifying mechanism 110, floor cleaner mechanism 510, or fragrancing mechanism 810, including the information provided by air purifying sensing mechanism 132, particulate sensing mechanism 134, dispenser sensing mechanism 512, or fragrancing sensing mechanism 832. For example, fragrancing controller 826 may adapt the concentration of fragrance used as a function ambient air quality, as indicated by particulate sensing mechanism 134.

In operation, the configuration of autonomously mobile air purifier and surface cleaner 830, transverses a floor under the power of mobile robotics mechanism 112 and provides air purifying by the action of air purifying mechanism 110, under the control of air purifying controller 124, surface cleaning under the control of floor cleaning controller 522, and fragrancing by the action of fragrancing 822, under the control of fragrancing controller 826 by use of the processed signals (not shown) of air purifying sensing mechanism 132, particulate sensing mechanism 134, dispenser sensing mechanism 512, and fragrancing sensing mechanism 832.

Figure 9:
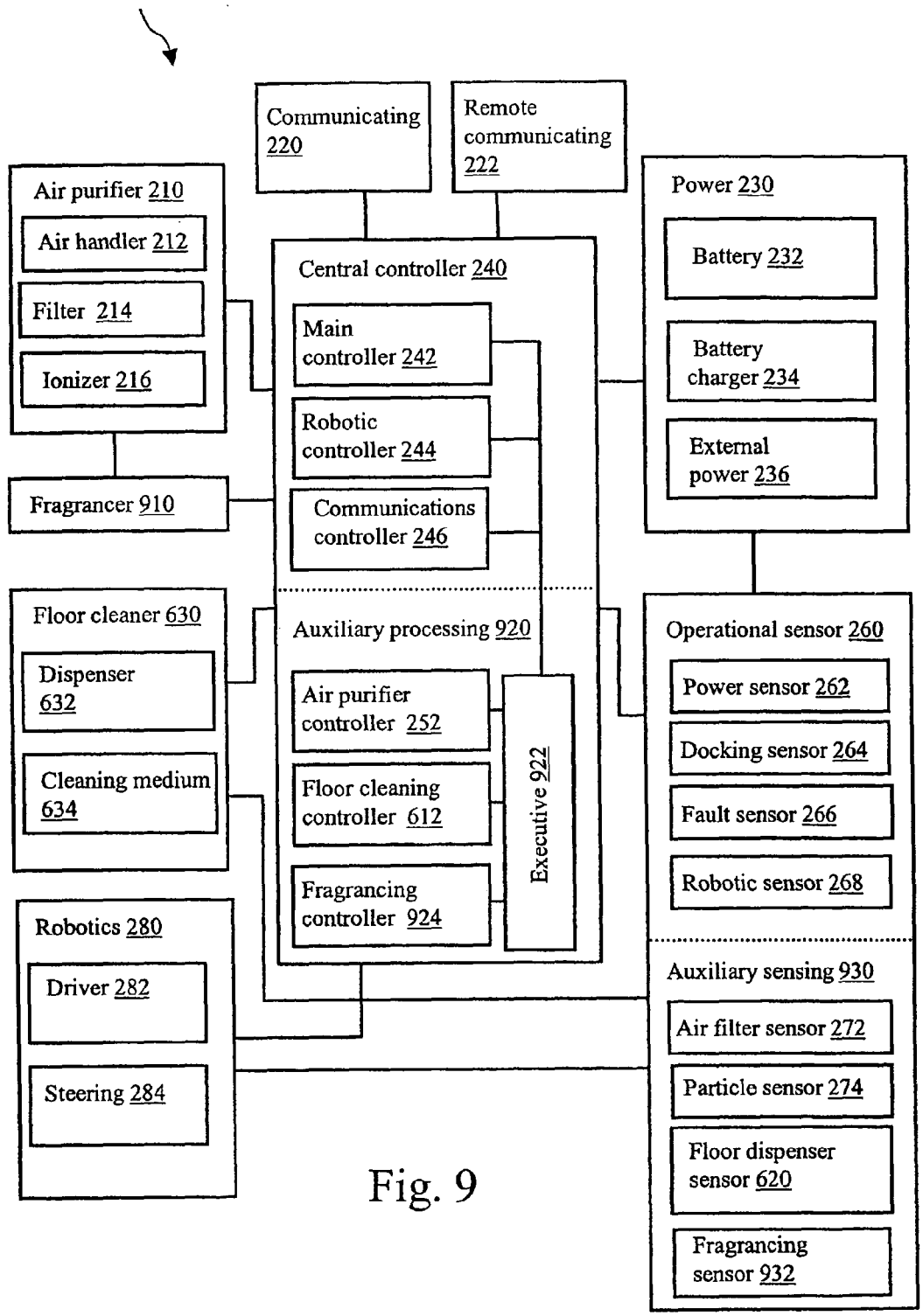
FIG. 9 is a schematic view of a twelfth embodiment of the autonomous cleaning device of the present invention.

FIG. 9 illustrates a system block diagram of a twelfth eleventh embodiment of an autonomously mobile air and surface cleaner and fragrancing system 900 that depicts the organization of system components of an especially preferred configuration of autonomously mobile air and surface cleaner and fragrancer 830. Autonomously mobile air and surface cleaner and fragrancing system 900 includes air purifier 210, which further includes air handler 212, filter 214, and ionizer 216. Autonomously mobile air purifier and surface cleaner system 600 also includes a fragrancer 910, communications interface 220, remote communications interface 222, and power source 230, which can include one or more of a rechargeable battery 232, battery charger 234, and external power 236. Autonomously mobile air and surface cleaner and fragrancing system 900 also includes central controller 240, which further contains main controller 242, robotic controller 244, and communications controller 246. Autonomously mobile air and surface cleaner and fragrancing system 900 also includes an auxiliary processor 920, which further includes air purifier controller 252, an executive controller 922, floor cleaning controller 614, and a fragrancing controller 924. Autonomously mobile air and surface cleaner and fragrancing system 900 also includes operational sensors 260, which further include power sensor 262, docking sensor 264, fault sensor 266, and robotic sensor 268. Autonomously mobile air and surface cleaner and fragrancing system 900 also includes auxiliary sensors 930, which further include air filter sensor 272, particle sensor 274, floor dispenser sensor 622, and fragrancing sensor 932. Autonomously mobile air and surface cleaner and fragrancing system 900 also includes robotics 280, which further includes a drive mechanism 282 and a steering or guidance system 284. Finally, autonomously mobile air and surface cleaner and fragrancing system 900 also includes floor cleaner mechanism 630, which further includes dispenser 632 and cleaning medium 634.

Fragrancer mechanism 910 is the means of imparting an aroma into the surrounding air and is, for example, a mechanism that allows one or more selected fragrant compound or oils to be evaporated and delivered into the ambient air through air handler 212. Auxiliary sensors 930 provide feedback for the air purification mechanisms, floor cleaning mechanisms, and fragrancing mechanisms of autonomously mobile air and surface cleaner and fragrancing system 900. Fragrancing sensor 932 within auxiliary sensing 930 provides feedback that indicates the extent of usage of fragrance (not shown) to determine whether it has been expended. Executive controller 922 within auxiliary processor 920 provides the supervisory control between air purifying controller 252, floor cleaning controller 612, and fragrancing controller 924. Fragrancing controller 924 handles the oversight and the control functions that coordinate the activities necessary for fragrancing, within the context of the other processes of autonomously mobile air purifier and surface cleaner and fragrancing system 900.

In operation, autonomously mobile air and surface cleaner and fragrancing system 900 performs the following functions in an autonomous manner: 1) status monitoring; 2) operator input monitoring; 3) robotics control; 4) air purification; 5) floor surface cleaning; and 6) fragrancing. In addition to the functionality listed above and described previously with regard to FIGS. 2 and 6, the further functional elements of FIG. 9 are described in operation as follows.

In perform the fragrancing control function, when a user enters fragrancing mode command on communications interface 220 or remote communications interface 222, central controller 240 commences the fragrancing mode. For example, when a command to change the fragrancing mode is entered, central controller 240 responds by reading fragrancing sensor 932 to determine an adequate fragrance supply level, and then sending the appropriate control signals to executive controller 922 and fragrancing controller 924, which activates fragrancer mechanism 910.

Figure 10:
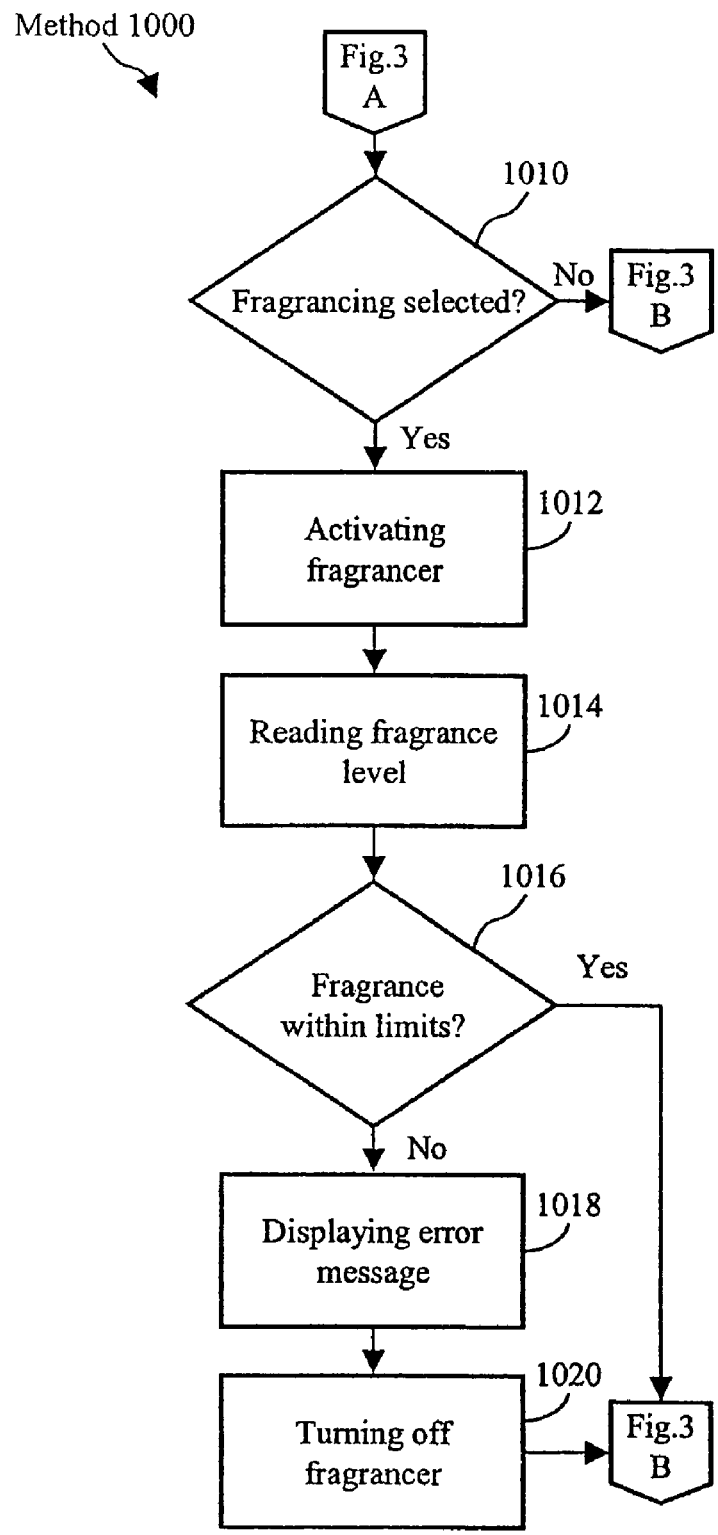
FIG. 10 is a flow chart illustrating the method of operation of the fragrancing mechanism of the autonomous cleaning device of FIG. 9.

Looking now at FIG. 10, a flow diagram of a method 1000 of enabling or activating the fragrancing function for autonomously mobile air and surface cleaner and fragrancing system 900 is illustrated that is employed in conjunction with the method 300 and indicated in FIG. 3 by blocks A and B. Method 1000 includes the following steps:

Step 1010: Fragrancing Selected?

In this decision step, which is also represented by block A in method 300 of FIG. 3, central controller 240 determines whether fragrancing has been selected via a user input or communications interface 220 or remote interface 222. If yes, method 1000 then proceeds to step 1012, but if no, method 1000 returns to method 300 and proceeds as previously described.

Step 1012: Activating Fragrancer

In this step, main controller 242 receives an interrupt, suspends its current operation, and sends a control signal to executive controller 922, which in turn instructs fragrance controller 924 to activate fragrancing mechanism 910. Method 1000 then proceeds to step 1014.

Step 1014: Reading Fragrance Level

In this step, fragrancing controller 924 reads fragrancing sensor 932 to determine the level of count of fragrance ranging to be dispensed by fragrancing mechanism 910. Method 1000 then proceeds to step 1016.

Step 1016: Fragrance Within Limits?

In this decision step, fragrancing controller 924 determines whether the status of the fragrance that was read in step 1014 is within proper predetermined or user-input limits. If yes, method 1000 then moves to method 300 and proceeds as previously described concerning method 300. If the fragrance level is outside the limits, method 1000 then proceeds to step 1018.

Step 1018: Displaying Error Message

In this step, fragrancing controller 924 communicates the status of fragrancer mechanism 910 to main controller 242 via executive controller 922, which instructs communications controller 246 to display an error message on communications interface 220 or remote interface 222. Method 1000 then proceeds to step 1020.

Step 1020: Turning Off Fragrancer

In this step, fragrancing controller 924 communicates the status of fragrancer mechanism 910 to main controller 242 via executive controller 922, which determines the most appropriate response based on the current operation mode and the other environmental conditions. For example, main controller 242 instructs fragrancing controller 924 discontinue the operation of fragrancer mechanism 910. Method 1000 returns to method 300 and proceeds as described previously regarding method 300.

Figure 11:
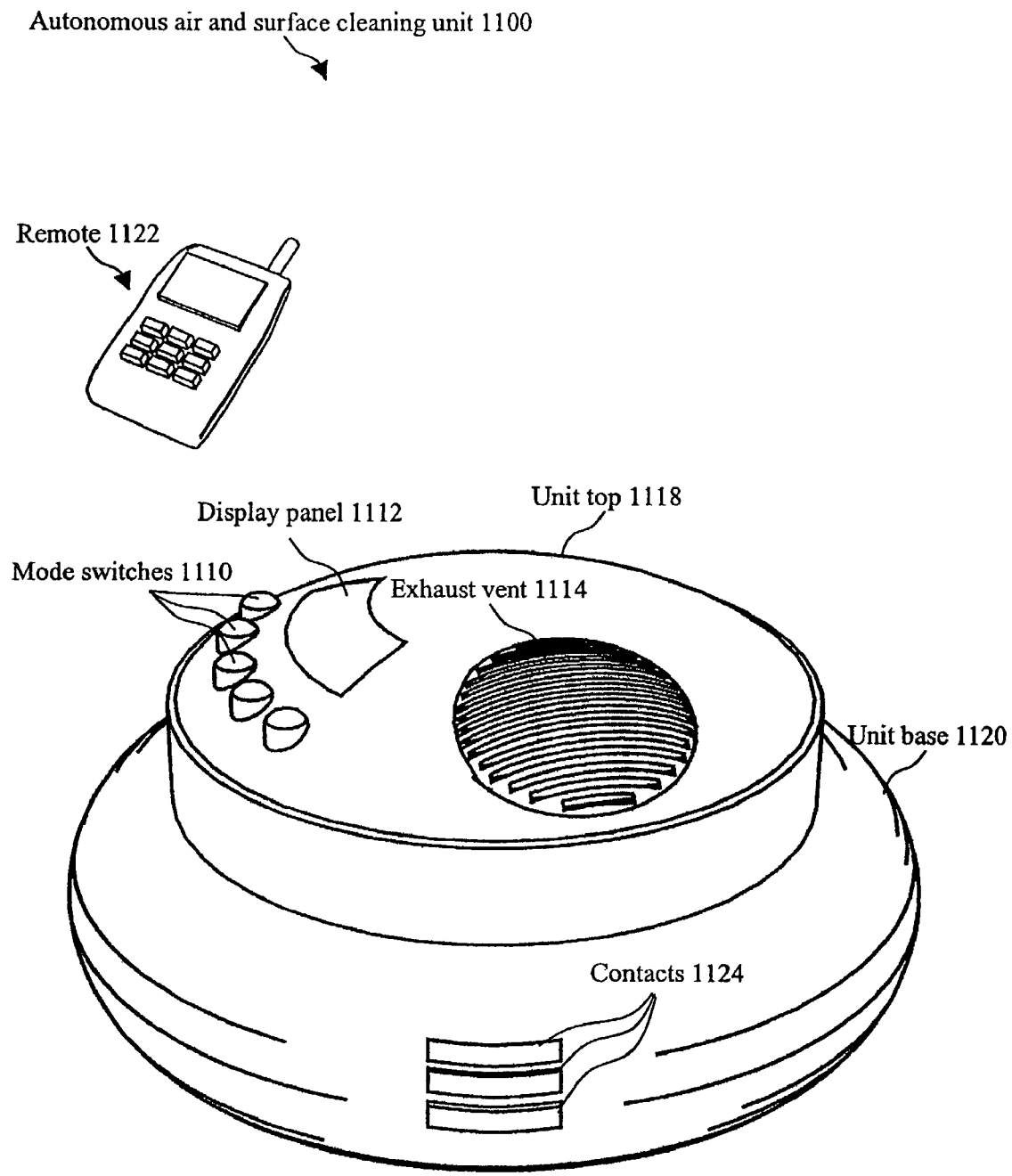
FIG. 11 is a perspective view of a thirteenth embodiment of the autonomous cleaning device of the present invention in a surface cleaning configuration.

FIG. 11 illustrate a thirteenth embodiment of an autonomous air and surface cleaning unit 1100 in its mobile surface cleaning mode. Autonomous air and surface cleaning unit 1100 in surface cleaning mode includes a plurality of mode switches 1110, a display panel 1112, an exhaust vent 1114, a unit top 1118, a unit base 1120, a remote control 1122 and a plurality of contacts 1124. Further, the unit 1100 can be configured with any of the previously described embodiments located within the unit 1100 to provide a selected number of the plurality of available functions for the unit 1100.

Mode switches 1110 are the means by which users select one of a number of pre-programmed operations for autonomous air and surface cleaning unit 1100, for example, air purification mode and surface cleaning mode. In addition, mode switches 1100 are context-specific within each mode selected and are used to provide additional functional inputs, i.e., the selection of the optional fragrancing mode within the air purification mode and the section of the specific type of fragrancing desired. Display panel 1112 is a small user display, for example, a liquid crystal device (LCD) or an organic or inorganic display (organic light-emitting diode (OLED) or light-emitting diode (LED), respectively). Exhaust vent 1114 is a louvered opening at the top of autonomous air and surface cleaning unit 1100 that is used to exhaust purified air in air cleaning-mode. Unit top 1118 forms the upper portion of autonomous air and surface cleaning unit 1100 and, in operation, when depressed, powers down the unit. In surface cleaning mode, unit base 1120 rests upon the surface to be cleaned, most often a floor. Unit base 1120 is the enclosure that contains the drive and control mechanisms (not shown) that propel and manage the operation of autonomous air and surface cleaning unit 1100. Remote 1122 is a wireless means of controlling autonomous air and surface cleaning unit 1100 that uses, for example, a radio frequency (RF) device. Unit contacts 1124 allow for automatic recharging of autonomous air and surface cleaning unit 1100 when it is used with a docking station 1300.

To initiate operation, a user powers-up autonomous air and surface cleaning unit 1100 by using the labeled "on" mode switch 1110. Thereafter, a user follows instructions displayed on display panel 1112 pursuant to the methods 300 and 700, shown and described previously, and selects the surface cleaning mode by using mode switches 1110. Alternatively, by following instructions, a user selects the surface cleaning mode by using remote 1122. Display panel 1112, or remote 1122 shows the selected mode and further prompts the user to select additional inputs, for example, to select a timed period of operation, to select a surface type, i.e., carpet or a hard floor, to select an operating speed, and optionally, to select from a number of pre-programmed options a route within the room for the surface cleaner to transverse, for example, a random route or a peripheral route around the perimeter of the room as described previously. Finally, the user selects the mode switch 1110 indicated by display panel 1112 to commence surface cleaning operation. Autonomous air and surface cleaning unit 1100 moves in the selected pattern and ceases motion under the following conditions: the set period of operation time has expired; autonomous air and surface cleaning unit 1100 has detected a fault or an impact; or any portion of unit top 1118 has been depressed (by the user, in operation or by remote control through use of remote 1122). Recharging the internal battery power supply of autonomous air and surface cleaning unit 1100 through contacts 1124 on unit base 1120 is accomplished using the docking station 1300 shown in FIG. 13.

Figure 12:
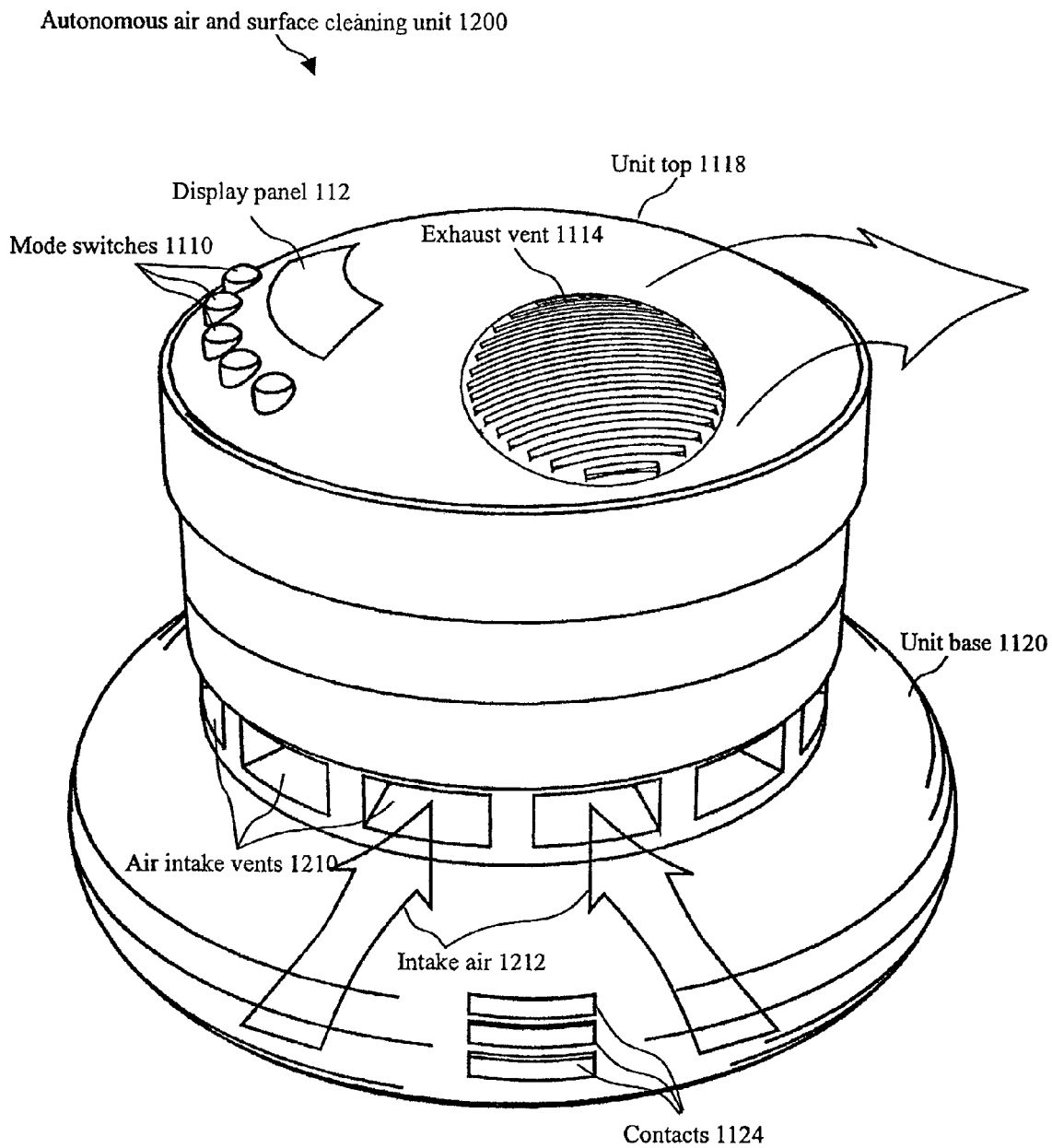
FIG. 12 is a perspective view of the autonomous cleaning device of FIG. 11 in an air cleaning configuration.

FIG. 12 illustrates the autonomous air and surface cleaning unit 1100 in its mobile air cleaning mode and includes, while in air cleaning mode, a plurality of air intake vents 1210. Air intake vents 1210 provide a source of intake air 1212, i.e. ambient room air, for the air treatment mechanism of autonomous air and surface cleaning unit 1100.

To initiate operation, a user powers-up autonomous air and surface cleaning unit 1100 by using the labeled "on" switch among mode switches 1110. Thereafter, by following instructions displayed on display panel 1112 in the manner utilizing the methods 300, 400 and 1000, shown and described previously, a user selects the air treatment mode by using mode switches 1110. Alternatively, by following instructions, a user selects the air treatment mode by using remote 1122. Display panel 1112 then shows the selected mode and further prompts the user to select additional inputs, for example, to select a timed period of operation, to select a fan speed, to optionally select a fragrance, to select the type of fragrance, to select an operating speed, and optionally, to select a route within the room for the unit to transverse, from a number of pre-programmed options, for example, a random route or a peripheral route around the perimeter of the room. Finally, the user selects the mode switch 1110 indicated by display panel 1112 to commence air treatment operation. Autonomous air and surface cleaning unit 1100 automatically deploys into the extended air treatment configuration shown in FIG. 12, by any number of ways, such as pneumatically, by solenoid action or by manual intervention by the user. This deployment thereby exposes air intake vents 1210. Autonomous air and surface cleaning unit 1100 then commences to move in the selected pattern to perform air purification, drawing in air from intake air 1212 and blowing out fresh air from exhaust vent 1114. Autonomous air and surface cleaning unit 1100 ceases motion under the conditions described with respect to the operation of unit 1100 in mobile surface cleaning mode. However, it is also contemplated that the unit 1100 can be operated simultaneously in both the surface cleaning mode in accordance with method 400, and in the air purification and fragrancing modes, in accordance with methods 700 and 1000.

Figure 13:
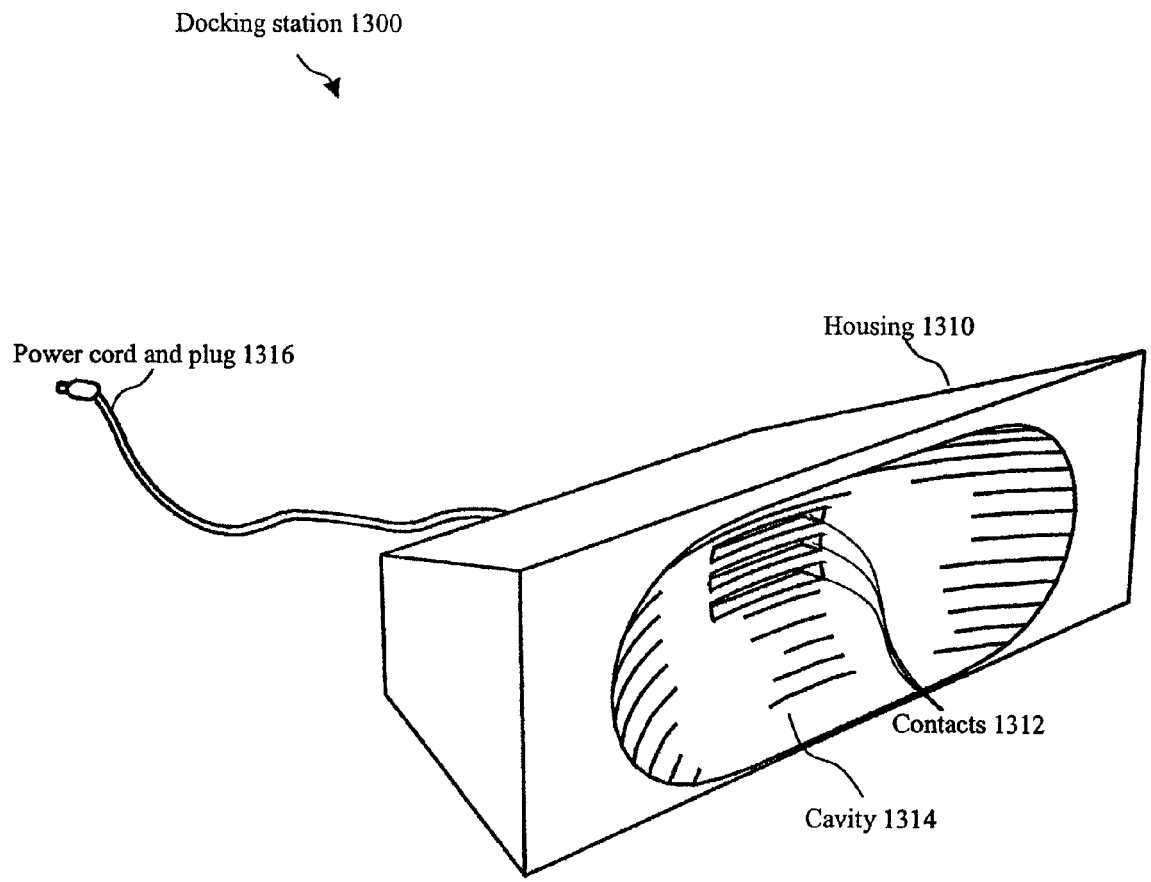
FIG. 13 is a perspective view of a docking station for use in conjunction with the autonomous cleaning device of FIG. 11.

Referring now to FIG. 13, a docking station 1300 is illustrated in that it includes a housing 1310, a plurality of contacts 1312, a cavity 1314 and a power cord and plug 1316. Docking station 1300 provides a means for autonomous recharging of autonomous air and surface cleaning unit 1100 in either the mobile surface cleaning mode or the mobile air cleaning mode. Housing 1310 is a standard, high-impact plastic or sheet metal, as is common for commercial household appliances. Contacts 1312 are concave electrical contacts that provide safe electrical connection with corresponding unit contacts 1124 on autonomous air and surface cleaning unit 1100. Cavity 1314 is a concave depression within housing 1310 that matches the convex curvature of unit base 1120 of autonomous air and surface cleaning unit 1100. Power cord and plug 1316 is the usual source of voltage for docking station 1300, but other sources can be utilized In operation of the preferred embodiment, docking station 1300 receives standard AC power, i.e., 110V 60 Hz, through power cord and plug 1316. Docking station 1300 transforms this power source to a low DC power source, for example +15 VDC, −15 DC, and ground potential, by standard power conversion methodologies, i.e., by means of transformers, voltage regulators, and energy storage devices, such as capacitors (not shown), as is well known by those skilled in the art. The low voltage, current-limited DC power source is then safely made available on contacts 1312. In use, autonomous air and surface cleaning unit 1100 navigates to docking station 1300 by means of a location signal, i.e., an infrared (IR) or radio frequency (RF) link, that emanates from a location signal generator (not shown) within docking station 1300. Autonomous air and surface cleaning unit 1100 then docks by fitting unit base 1120 fits within cavity 1314. Autonomous air and surface cleaning unit 1100 then makes electrical connection with contacts 1312 with its corresponding unit contacts 1124. Those skilled in the art will appreciate that a locating mechanism using either an infrared (IR) or radio frequency (RF) technology is well known. Alternately, the unit 1100 can determine the location by the path it had taken to its current location.

Figure 14:
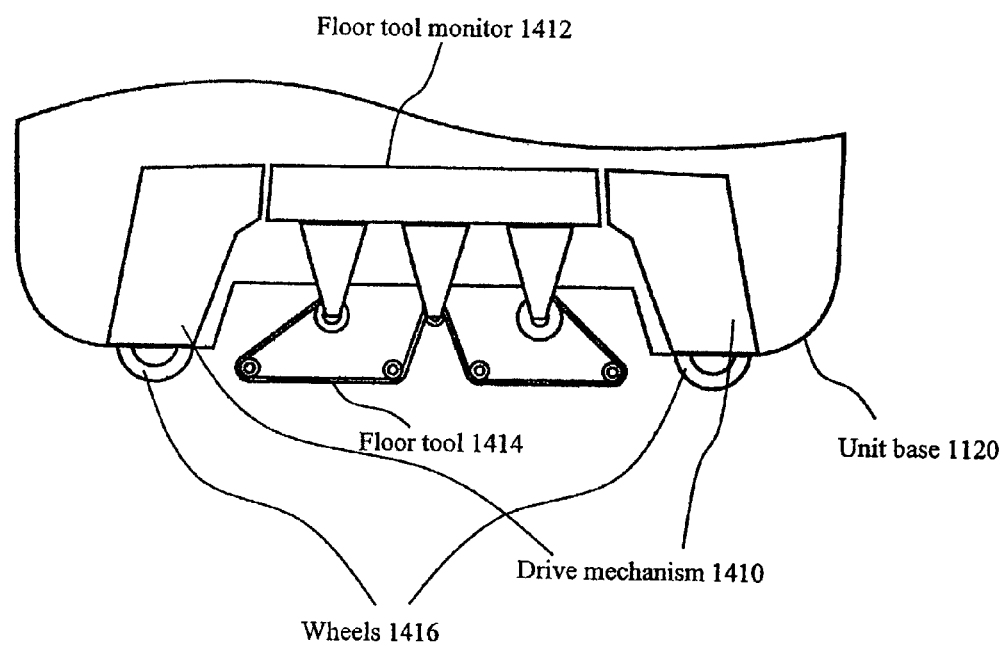
FIG. 14 is a partially broken away, side plan view of a mobile robotics mechanism and floor cleaning mechanism of the autonomous cleaning device of FIG. 11.
Figure 15:
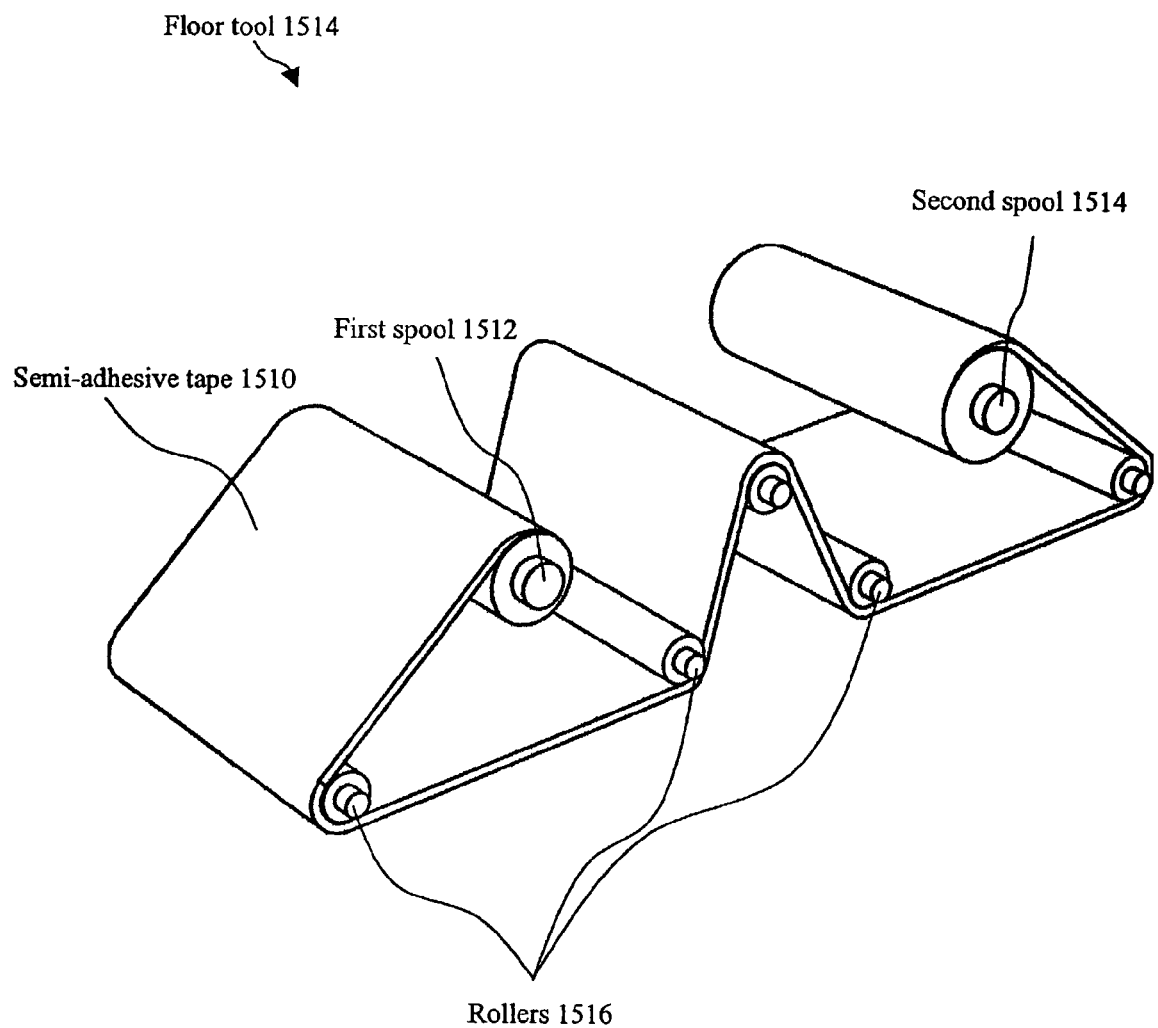
FIG. 15 is a perspective view of the floor cleaning mechanism of FIG. 14.

Looking now at FIGS. 14 and 15, a floor cleaning mechanism 1400 for the unit 1100 is shown that includes a drive mechanism 1410, a floor tool monitor 1412, a floor tool 1414, and wheels 1416. Floor cleaning mechanism 1400 provides a means of removal of contaminants, such as surface particulates for autonomous recharging of autonomous air and surface cleaning unit 1100. Floor tool 1414 provides the surface cleaning action. Floor tool monitor 1412 determines the capacity of floor tool 1414 cleaning element, and determines when it is expended. Drive mechanism 1410 encompasses the electro-mechanical powering, steering, and braking functions that are controlled by the unit 1100, such as by in mobile robotics mechanism 112 and that guide and propel autonomous air and surface cleaning unit 1100 by means of wheels 1416.

Floor tool 1414 includes a semi-adhesive tape 1510, a first spool 1512, a second spool 1514, and a plurality of rollers 1516. Floor tool 1414 provides the surface cleaning action of autonomous air and surface cleaning unit 1100 by direct contact with surface contaminants. Semi-adhesive tape 1510 equally collects contaminants in both forward and reverse directions. Rollers 1516 are the means of managing the dispensing of semi-adhesive tape 1510 between first spool 1512 and second spool 1514. Rollers 1516 also provide tension to maintain the contact of semi-adhesive tape 1510 with the surface to be cleaned. For a given length of material, semi-adhesive tape 1510 is fresh in the forward direction, but equally fresh if the same length is moved in the opposite direction. Semi-adhesive tape 1510 is a consumable; when the tape is expended, it is replaced. For example, first spool 1512 is the source of tape 1510, and as autonomous air and surface cleaning unit 1100 is propelled, first spool 1512 rotates counter-clockwise and dispenses around rollers 1516, whereupon it comes into contact with the contaminated surface and thereby lifts dust and other small particulates and finally winds on second spool 1514. In reverse, the directions in the foregoing discussion are inverted. The central processor unit within autonomous air and surface cleaning unit 1100 accounts for the usage of tape 1510 and controls the advance and retraction of the tape, by alternating the overall unit forward and reverse movement, until the tape is expended.

In operation, autonomous air and surface cleaning unit 1100 transverses a floor surface, under power of drive mechanism 1410, by means of wheels 1416. The result of this motion causes floor tool 1414 to advance fresh cleaning element, such as a semi-adhesive "tape," between its spools 1512 and 1514. Floor tool monitor 1412 constantly keeps track of the capacity of the cleaning element, i.e., the position of the tape on the spool, and provides feedback to the central processing unit regarding which segments of the tape have been expended. When the cleaning element of floor tool 1414 is completely expended, autonomous air and surface cleaning unit 1100 ceases to operate and indicates to the user, via a message on display panel 1112, the need to replace the cleaning element.

Figure 16:
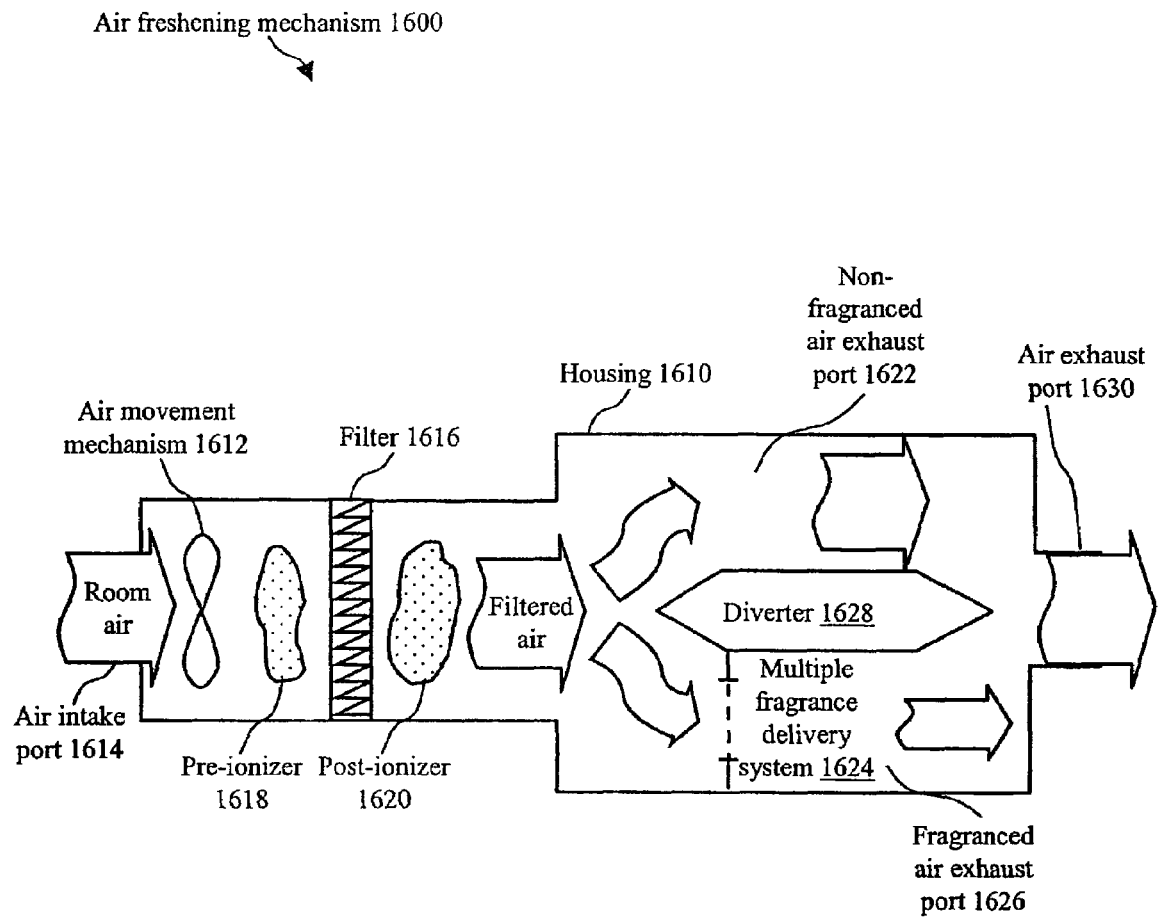
FIG. 16 is a schematic view illustrating the operation of the autonomous cleaning device in the air cleaning configuration of FIG. 12.

FIG. 16 is a functional diagram of an air freshening mechanism 1600 that can be disposed within the unit 1100 and provides air purification in combination with fragrancing within autonomous air and surface cleaning unit 1100. Air freshening mechanism 1600 includes a housing 1610, within which is installed an air movement mechanism 1612 for drawing airflow into housing 1610 via an air intake port 1614 that is in communication with air intake units 1210. Airflow generated by air movement mechanism 1612 pushes against and through a filter 1616, which is located on the exhaust side of air movement mechanism 1612. Arranged between air movement mechanism 1612 and filter 1616 is a pre-ionizer 1618, and arranged on the exhaust side of filter 1616 is a post-ionizer 1620. A first portion of the filtered air from the exhaust side of filter 1616 exits housing 1610 through air exhaust port 1630 via a non-fragranced air exhaust port 1622, and a second portion of the filtered air from the exhaust side of filter 1616 passes through a multiple fragrance delivery system 1624 and, subsequently, exits housing 1610 through air exhaust port 1630 via a fragranced air exhaust port 1626. The air exhaust port 1530 is located within the limit in communication with the exhaust port 1114 on the unit top 1118. A diverter 1628 forms the physical separation between the two airflows through non-fragranced air exhaust port 1622 and fragranced air exhaust port 1626.

Air movement mechanism 1612 is, for example, in a preferred embodiment, a standard, commercially available, axially mounted multi-speed DC electric fan for pushing air through filter 1616. Air movement mechanism 1612 is capable of providing, for example, 30-100 cubic feet/minute (CFM) of airflow. Those skilled in the art will appreciate that the power supply (not shown) and electronic control (not shown) of a standard, multi-speed DC electric fan is well known. In an alternative embodiment, a squirrel cage fan may be used for pulling (rather than pushing) air through filter 1616. However, an axially mounted fan is preferred, because it creates higher head pressure against filter 1616, as compared to that of a squirrel cage fan.

In a preferred embodiment, filter 1616 is a conventional trapping filter that removes particulates form the air steam. For example, filter 1616 is a small footprint filter that has a clean air delivery rate (CADR) rating of 80 or less, a pressure drop of less than 10-12 Pascals, and an ozone emission of less than 0.05 ppm. CADR is an industry standard filter rating that is based on how much material is removed from the air in a single pass through a filter. Filter 1616 includes a screen that is fine enough to filter out the desired particulates. The finer the particle, the finer the screen and, therefore, the greater the pressure needed to push air through the screen, which affects the possible CFM and the rate of air exchange in the room. In the case of air freshening mechanism 1600, if, for example, air movement mechanism 1612 provides approximately 90 CFM entering filter 1616, approximately 55 CFM of airflow exits filter 1616.

Pre-ionizer 1618 and post-ionizer 1620 are each optional and serve as precipitating filter mechanisms used to enhance the function of filter 1616. Pre-ionizer 1618 and post-ionizer 1620 are, in a preferred embodiment, standard, commercially available needle ionizers that use high voltage to create negative ions. These electrons accumulate on an exposed electrode, or needle, and attract oxygen molecules. At this point, the oxygen molecules become negative ions that, in turn, attract and attach to airborne particles. When enough negative ions attach to a particle, it becomes too heavy to float in the air and drops to the ground or others surface, in a process known as agglomeration, which effectively removes it from the circulating air. Those skilled in the art will appreciate that the high voltage power supply (not shown) and electronic control (not shown) for such a standard needle ionizer device are well known, such that it is not necessary to describe them in detail in this application.

Air freshening mechanism 1600 of the present invention generally provides fragrancing to the user by dispensing the fragrance, such as by using fragrancer 910, into the exhaust stream of the device 1100. One example of a suitable mechanism for fragrancer 910 is illustrated in FIG. 16 is multiple fragrance delivery system 1624. Multiple fragrance delivery system 1624 is representative of a single or multi-fragrance delivery system that allows the user to turn on or off the selected fragrance. Multiple fragrance delivery system 1624 includes, for example, one or more supplies of fragrance oil, compound, gel and a capillary system for evaporating the oil into the airflow. Further details of multiple fragrance delivery system 1624 are found in reference to FIGS. 17A-17E.

Diverter 1628 is representative of any well-known device, such as a baffle or louver, for directing airflow along one or more airflow paths. In the case of air freshening mechanism 1600, diverter 1628 directs a portion of filtered air from the exhaust side of filter 1616 toward non-fragranced air exhaust port 1622 and also toward multiple fragrance delivery system 1624, which supplies fragranced air exhaust port 1626. The design of diverter 1628 is such that in a preferred embodiment 0-10% of the filtered air exiting filter 1616 is directed into multiple fragrance delivery system 1624 and, subsequently, exits fragranced air exhaust port 1626. Consequently, 90-100% of the filtered air exiting filter 1616 is directed toward non-fragranced air exhaust port 1622. However, the selected percentages of these air flows can also be altered as desired depending upon the particular use the unit 1100 is designed for, such as by using a movable baffle (not shown) capable of diverting between 0% and 100% of the filtered air flow through either exhaust port 1622 or 1626.

In a preferred embodiment, regardless of the CFM capability of air freshening mechanism 1600, the design of diverter 1628 limits the maximum airflow entering into multiple fragrance delivery system 1624 and, subsequently, limits the exiting fragranced air exhaust port. In this way, the maximum quantity of fragranced air delivered into the environment is controlled to an acceptable level (i.e., non-offensive level) and is not dependent on the overall CFM capability of air freshening mechanism 1600.

The air delivery rate vs. noise specification of air freshening mechanism 1600 is optimized to ensure an air delivery rate suitably high for achieving a preferred turn-over rate of four exchanges of air per hour in a 10×10 ft to 10×12 ft room, while at the same time maintaining a suitably low maximum noise specification, such as a noise specification not exceeding 50 decibels (dB). This optimization establishes an ideal performance on a "high setting" for a multi-speed fan in mechanism 1612 at an airflow of approximately 55 CFM through the filter 1616 at a noise rating of <40 dB. Taking these specifications into account, in order to deliver an acceptable overall CADR rating for air freshening mechanism 1600, the electric fan of air movement mechanism 1612 operates with a <100 CFM motor in combination with either filter 1616 being a large footprint, high-pressure drop filter or, preferably, filter 1616 being a small footprint, low-pressure drop (less than 12 pascals) filter. Additionally, in order for air freshening mechanism 1600 to deliver an overall acceptable CADR rating, air movement mechanism 1612 and filter 1616 operate in combination with pre-ionizer 1618 and post-ionizer 1620, which enhance the function of filter 1616 and thereby improve the overall CADR rating. Assuming a multi-speed fan in mechanism 1612, the result is an air freshening mechanism 1600 that provides a "low setting" specification of, for example, 30 CFM at 30 dB; a "medium setting" specification of, for example, 40 CFM at 35 dB; and a "high setting" specification of, for example, 50-55 CFM at 40 dB.

In operation, one or more supplies 1714*a-c* of fragrance oil are installed within multiple fragrance delivery system 1624 of air freshening mechanism 1600. The user then selects a desired fragrance, or no fragrance at all, and activates air freshening mechanism 1600, whereby air movement mechanism 1612, pre-ionizer 1618, and post-ionizer 1620 are activated. In one example, air movement mechanism 1612 is activated and, thus, draws air into air freshening mechanism 1600 via air intake port 1614. Air movement mechanism 1612 pushes approximately 90 CFM of airflow into filter 616. Pre-ionizer 1618 removes particles from the airflow, as air passes from air movement mechanism 1612 toward the intake of filter 1616. Filter 1616 then performs an additional filtering operation by trapping particulates that are not removed by the action of pre-ionizer 1618. Approximately 55 CFM of filtered air exits the exhaust side of filter 1616 and, subsequently, passes by post-ionizer 1620, which removes additional particles remaining in the airflow, as a final air purification mechanism. As a result, filtered air is directed by diverter 1628 toward non-fragranced air exhaust port 1622 and multiple fragrance delivery system 1624. The vast majority of airflow exits air exhaust port 1630 via non-fragranced air exhaust port 1622, and a much smaller controlled amount of airflow passes through multiple fragrance delivery system 1624 and, subsequently, exits air exhaust port 1630 via fragranced air exhaust port 1626. In this example, if 55 CFM of filtered air exits the exhaust side of filter 1616, no less than 90%, which is 49.5 CFM of airflow is directed to non-fragranced air exhaust port 1622 by diverter 1628 and up to 10%, which is 5.5 CFM of airflow passes through multiple fragrance delivery system 1624 and, subsequently, exits air exhaust port 1630 via fragranced air exhaust port 1626.

FIGS. 17A-17E illustrate a capillary system 1700 for providing a selection of multiple fragrances in accordance with the invention. Capillary system 1700 is formed as a wick-based system that incorporates a capillary member for delivering fragrance to the airflow. More specifically, capillary system 1700 includes an elongated, thin, flat substrate 1710 formed of, for example, molded plastic or glass. Arranged along the lower surface of substrate 1710 are one or more capillary regions 1712 associated with one or more fragrance supplies 1714, respectively. Each fragrance supply 1714 further includes a wick 1716, which is positioned in direct contact with the lower surface of substrate 1710.

Capillary regions 1712 are representative of a wickable surface for enhancing vaporization of the fragrance oil into the air stream of air freshening mechanism 1600. Capillary regions 1712 are, in a preferred embodiment, 1 to 2 in$^2$ in area and are formed by one or more exposed capillary pathways (i.e., mechanical grooves) that are printed, etched, or molded into the surface of substrate 1710. The critical characteristics of the capillary pathways may be optimized to accommodate the surface tension of specific fragrance formulations (e.g., scented oil). These characteristics include, for example, the angle of the groove walls, the sharpness of the lower corner, and a minimum depth specification, among others.

In a preferred embodiment, capillary regions 1712 are formed according to the principles and structures described in commonly-assigned U.S. patent application Ser. No. 10/266,798 (the '798 application) entitled, "Wick-based delivery system with wick having small porosity sections," assigned to SC Johnson & Son, Inc., of Racine, Wis., which is incorporated herein by reference in its entirety. The '798 patent application describes an evaporative device that includes a container for holding a liquid that has a porous wick extending through an opening, such that a portion of the wick contacts the liquid held within the container and a portion of the wick is exposed to the ambient environment, wherein the wick transfers the liquid from the container to the ambient air, and a portion of the wick is in communication with a surface of a capillary member. The surface has one or more exposed capillary pathways along which liquid, transferred by the wick from the container, is drawn by capillary action for dispersion to the ambient air.

An example of a wick-based fragrance supply suitable for use as fragrance supply 1714 is a Glade® brand Wisp™ fragrance oil refill bottle, manufactured by SC Johnson & Son, Inc. of Racine, Wis. Example fragrances include cinnamon, apple, citrus, vanilla, floral fragrances, and tropical fruit fragrances. In the case where the capillary pathways of capillary regions 1712a-c are optimized for use with the Glade® brand Wisp™ fragrance oil, the groove walls have a specified angle, the lower corner has a specified angle, and the groove depth is at a specified minimum.

Wicks 1716a, 1716b, and 1716c of fragrance supplies 1714a, 1714b, and 1714c, respectively, are arranged linearly and in contact with the lower surface of substrate 1710. A capillary region 1712a is associated with wick 1716a, a capillary region 1712b is associated with wick 1716b, and a capillary region 1712c is associated with wick 1716c. Only one wick 1716a-c is in contact with and, therefore, engaged with, its associated capillary region 1712a-c at one time. This is accomplished by the adjustment of the relative linear position of substrate 1710 to fragrance supplies 1714a, 1714b, and 1714c and wicks 1716a, 1716b, and 1716c.

Figure 17A:
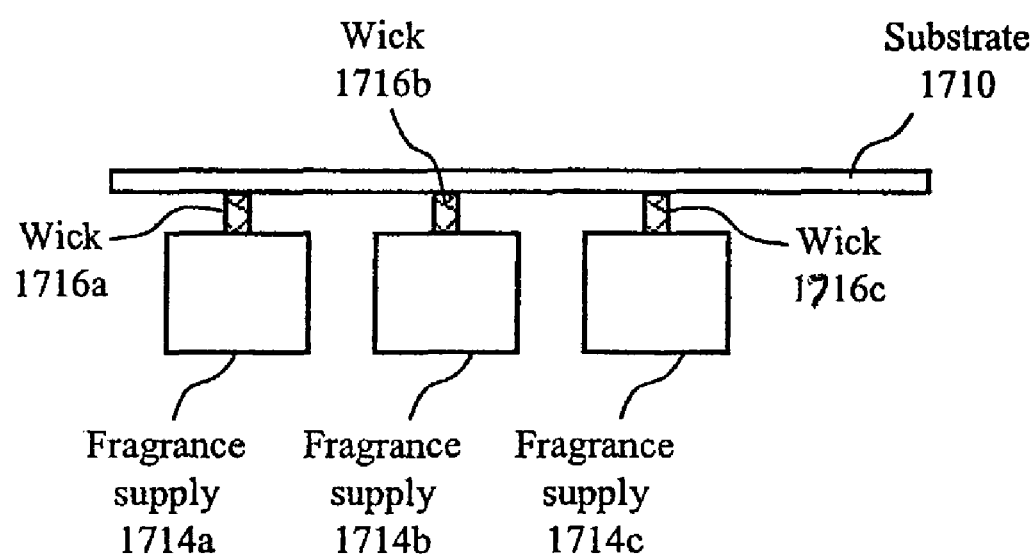
FIG. 17A is a schematic view of a fragrance mechanism of the autonomous cleaning device of FIG. 12.
Figure 17B:
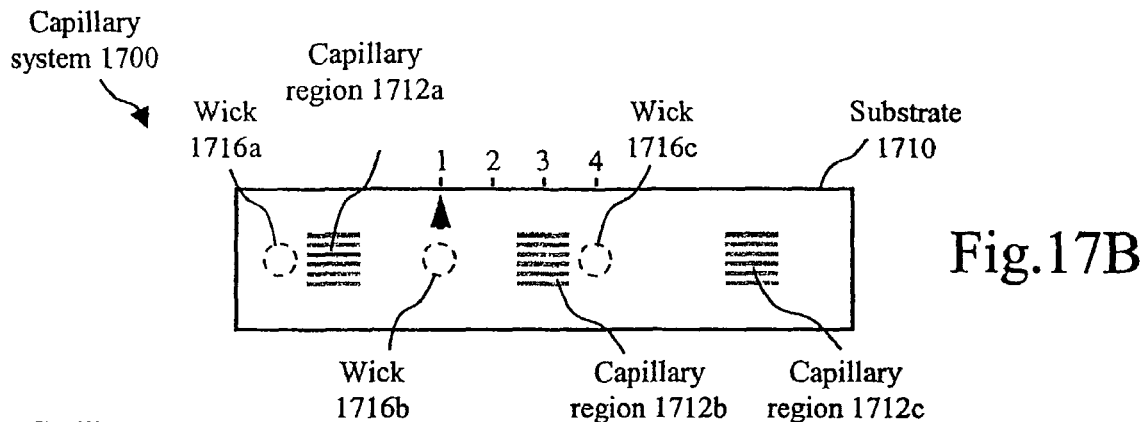
FIGS. 17B-17E are schematic views illustrating the fragrancing mechanism of FIG. 17A in various operating configurations.
Figure 17C:
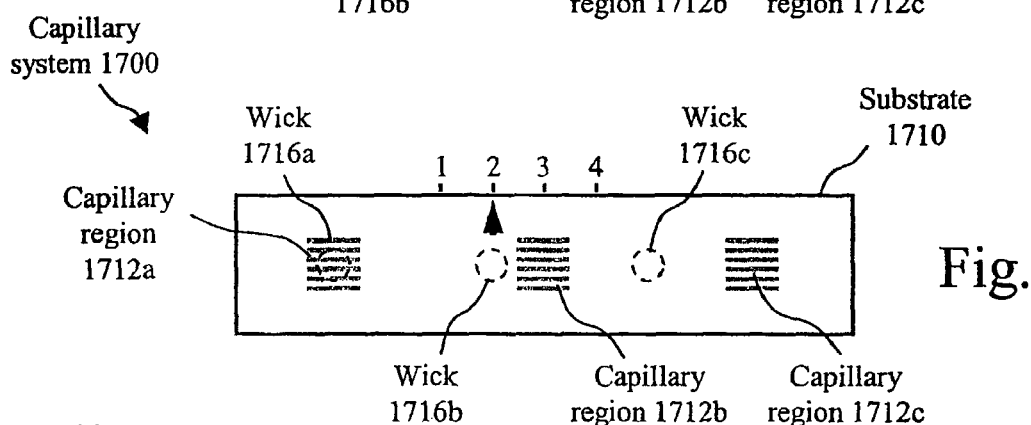
Figure 17D:
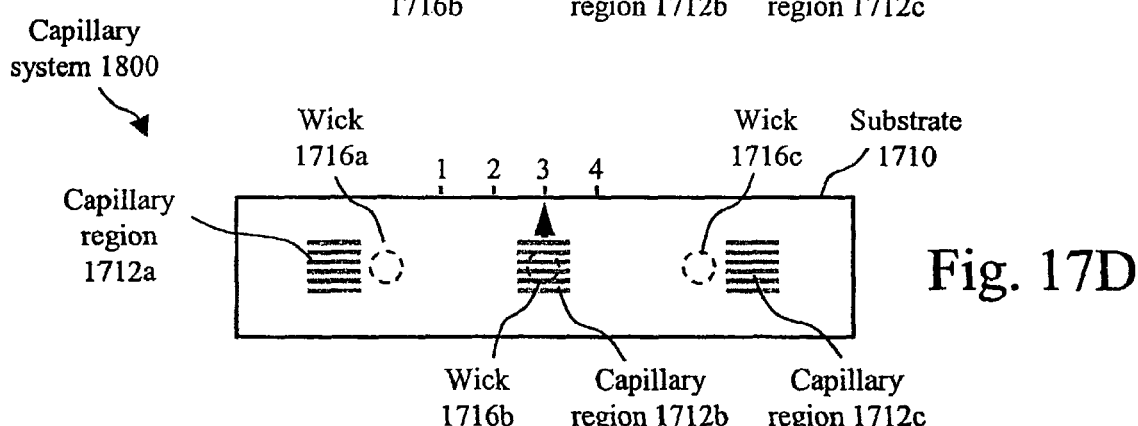
Figure 17E:
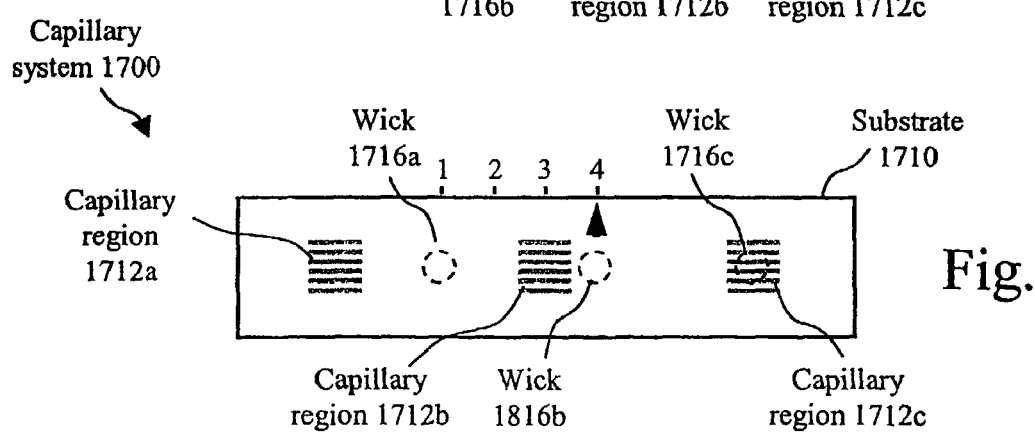

In a particularly preferred embodiment, substrate 1710 is slideably installed within housing 1610 of air freshening mechanism 1600 and aligned with and in contact with wicks 1716a, 1716b, and 1716c of fragrance supplies 1714a, 1714b, and 1714c, respectively, which are also, at least partially installed within housing 1610. FIG. 17B illustrates a first position, wherein none of wicks 1716a, 1716b, or 1716c is engaged with its associated capillary regions 1712a, 1712b or 1712c, respectively, and, thus, no fragrance is selected, which thereby provides a means for the user to turn off fragrancing within air freshening mechanism 1610. FIG. 17C illustrates a second position, wherein wick 1716a is engaged with capillary region 1712a and wicks 1716b and 1716c are not engaged with capillary regions 1712b and 1712c, respectively, and, thus, the fragrance of fragrance supply 1714a is selected. FIG. 17D illustrates a third position, wherein wick 1716b is engaged with capillary region 1712b and wicks 1716a and 1716c are not engaged with capillary regions 1712a and 1712c, respectively, such that the fragrance of fragrance supply 1714b is selected. FIG. 17E illustrates a fourth position, wherein wick 1716c is engaged with capillary region 1712c and wicks 1716a and 1716b are not engaged with capillary regions 1712a and 1712b, respectively, such that the fragrance of fragrance supply 1714c is selected.

In operation, in the second, third, and fourth positions, as air flows across the surface of substrate 1710 and, thus, across capillary regions 1712a, 1712b, and 1712c, the liquid is transferred by wicks 1716a, 1716b, or 1716c, respectively, from fragrance supplies 1714a, 1714b, or 1714c, respectively, and drawn by the capillary action of capillary regions 1712a, 1712b or 1712c, respectively, for dispersion by evaporation to the ambient air via fragranced air exhaust port 1626. The user may select a fragrance mode command on switches 1110 or on remote control 1122 causing substrate 1710 to move relative to fragrance supplies 1714 within capillary system 1700.

With reference to FIGS. 17A-17E and capillary system 1700, the selection of one of the multiple fragrances or no fragrance at all is performed via automated manipulation of the elements of multiple fragrance delivery system 1624 by a standard motion control system (not shown) provided within air freshening mechanism 1600 and, thus, the user uses electronic control to select the desired mode via switches 1110 or remote control 1122. The inclusion of a motion control system within air freshening mechanism 1600 also allows the unit to be timer controlled. For example, air freshening mechanism 1600 includes well-known electronics (not shown) that allow the user to select when air freshening mechanism 1600 is automatically turned on or off and also to automatically select a given fragrance at a given time of day for a given amount of time.

Additionally, capillary system 1700, i.e., the physical assembly that forms multiple fragrance delivery system 1624, is easily removable from air freshening mechanism 1600 and unit 1100, such that the user can easily and conveniently replace the fragrance supply i.e., fragrance supplies 1714a-c, when they are depleted.

Multiple fragrance delivery system 1624 is not limited to the above-mentioned example combinations. Those skilled in the art will appreciate that multiple fragrance delivery system 1624 may be designed with a capillary system that provides any number of combinations of fragrance levels and fragrance blends. In particular, other suitable configurations for the multiple fragrance delivery system 1624 are disclosed in commonly-assigned U.S. Provisional Patent Application Ser. No. 60/630,344, entitled "Systems For And Methods Of Providing Air Purification In Combination With Fragrancing," which is incorporated by reference herein in its entirety.

Various alternatives are contemplated as being within the scope of the following claims particularly pointing out and distinctly claiming the subject matter regarded as the invention.

We hereby claim:

1. A cleaning device comprising; a) an air purification system disposed within a housing; b) a surface cleaning system disposed within the housing; c) a movement mechanism disclosed within the housing and capable of moving the housing containing the air purification system and the surface cleaning system; d) a sensor system configured to monitor performance of at least one of the air purification system and the surface cleaning system; and e) a control system connected to and configured to control the operation of the air purification system, the surface cleaning system and the movement mechanisms in a generally autonomous fashion based on feedback received from the sensor system regarding performance of the at least one of the air purification system and the surface cleaning system, the control system configured to control operation of the other of the at least one of the air purification system and the surface cleaning system in response to the monitored performance of the at least one of the air purification system and the surface cleaning system.

2. The device of claim 1 further comprising a fragrance dispensing system disposed within the housing and operably connected to the air purification system and the control system.

3. The device of claim 1 wherein the control system is operatively connected to a user interface.

4. The device of claim 3 wherein the user interface is disposed on an exterior of the housing.

5. The device of claim 1 wherein the control system is operatively connected to the sensor system and the sensor system includes a plurality of sensors.

6. The device of claim 5 wherein the sensors are configured to detect conditions inside the housing.

7. The device of claim 5 wherein the sensors are configured to detect conditions outside the housing.

8. The device of claim 5 wherein the control system is configured to vary the operation of the air purification system, and the surface cleaning system, and the movement system in response to signals sent from the plurality of sensors associated with another of the air purification system, the surface cleaning system, and the movement system.

9. A method for cleaning an area, the method comprising the steps of: a) providing a cleaning device including an air purification system disposed within a housing, a surface cleaning system disposed within the housing, a movement system disposed within the housing and capable of moving the housing containing the air purification system and the surface cleaning system around the area, and a control system connected to and configured to control the operation of the air purification system, the surface cleaning system and the movement system in a generally autonomous manner; b) selecting a mode of operation for the device; c) operating the device in the selected mode of operation; d) automatically monitoring performance of at least one of the air purification system and the surface cleaning system; and e) automatically altering operation of the other of the least one of the air purification system and the surface cleaning system in response to monitored performance of the at least one of the air purification system and the surface cleaning system.

10. The method of claim 9 wherein the step of selecting the mode of operation for the device comprises inputting the mode of operation into the control system.

11. The method of claim 10 wherein the step of inputting the desired mode of operation comprises employing a user interface operatively connected to the control system.

12. The method of claim 9 wherein the step of selecting the mode of operation comprises selecting an air purification mode of operation.

13. The method of claim 12 further comprising the step of varying the air purification mode of operation in response to signals sent from sensors operatively connected to the control system.

14. The method of claim 12 further comprising the step of selecting an air fragrancing mode of operation subsequent to selecting the air purification mode of operation.

15. The method of claim 12 further comprising the step of varying the air purification mode of operation in response to signals sent from a user interface operatively connected to the control system.

16. The method of claim 9 wherein the step of selecting the mode of operation comprises selecting a surface cleaning mode of operation.

17. The method of claim 16 further comprising the step of varying or stopping the surface cleaning mode of operation in response to signals sent from sensors operatively connected to the control system.

18. The method of claim 16 further comprising the step of varying the surface cleaning mode of operation in response to signals sent from the user interface operatively connected to the control system.

19. The method of claim 9 wherein the step of selecting a mode of operation comprises selecting a movement mode of operation.

20. The method of claim 19, further comprising the step of A method for cleaning an area, the method comprising the steps of:
   a) providing:
      a cleaning device including a housing containing at least one of: an air purification system, a surface cleaning system, and a fragrancing system;
      a movement system disposed within the housing and capable of moving the housing around an area; and
      a control system connected to and configured to control the movement system in a generally autonomous manner;
   b) selecting a mode of operation for the device;
   c) operating the device in the selected mode of operation;
   d) automatically monitoring performance of at least one of the air purification system and the surface cleaning system; and
   e) varying or stopping the movement mode of operation in response to signals sent from sensors operatively connected to the control system.

* * * * *